(12) United States Patent
Krumanaker et al.

(10) Patent No.: US 9,089,326 B2
(45) Date of Patent: Jul. 28, 2015

(54) DUAL STAPLE CARTRIDGE FOR SURGICAL STAPLER

(75) Inventors: David T. Krumanaker, Cincinnati, OH (US); Robert J. Simms, Liberty Township, OH (US); Edit Goldberg, Zichron Yaaqov (IL); Thomas A. Osborne, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 869 days.

(21) Appl. No.: 13/267,922

(22) Filed: Oct. 7, 2011
(Under 37 CFR 1.47)

(65) Prior Publication Data
US 2013/0087599 A1    Apr. 11, 2013

(51) Int. Cl.
| | | |
|---|---|---|
| *A61B 17/068* | (2006.01) | |
| *A61B 17/072* | (2006.01) | |
| A61B 17/064 | (2006.01) | |
| A61B 17/29 | (2006.01) | |

(52) U.S. Cl.
CPC ......... *A61B 17/072* (2013.01); *A61B 17/07292* (2013.01); *A61B 2017/0645* (2013.01); *A61B 2017/07228* (2013.01); *A61B 2017/07271* (2013.01); *A61B 2017/2927* (2013.01)

(58) Field of Classification Search
CPC ........... A61B 17/068; A61B 17/06804; A61B 17/064072; A61B 2017/0725; A61B 2017/07271; A61B 17/072
USPC ................. 227/175.1–4, 176.1, 177.1, 178.1, 227/179.1, 180.1, 181.1, 182.1
See application file for complete search history.

(56) References Cited

U.S. PATENT DOCUMENTS

| | | |
|---|---|---|
| 2,303,131 A | 11/1942 | Morgan |
| 3,364,200 A | 1/1968 | Ashton et al. |

(Continued)

FOREIGN PATENT DOCUMENTS

| | | |
|---|---|---|
| CA | 481943 | 2/1947 |
| EP | 0 306 298 | 3/1989 |

(Continued)

OTHER PUBLICATIONS

International Search Report dated Jun. 6, 2013 for Application No. PCT/US2012/058969.

(Continued)

*Primary Examiner* — Thanh Truong
*Assistant Examiner* — Xavier A Madison
(74) *Attorney, Agent, or Firm* — Frost Brown Todd LLC

(57) ABSTRACT

A surgical stapler includes and end effector configured to receive an upper staple cartridge and a lower staple cartridge. The lower staple cartridge includes staple drivers disposed at a non-perpendicular or oblique angle. The staple drivers may be oppositely angled relative to the perpendicular. The staple drivers may further be coupled to an actuation member that pivots the staple drivers to the perpendicular prior to stapling. The actuation members may be actuated by the firing bar and/or by a wedge sled. The upper staple cartridge may also include angled staple drivers that are pivotable to the perpendicular. The upper staple cartridge and/or the lower staple cartridge may also include staple forming pockets. Alternatively, one staple driver may be perpendicular and second staple driver may be at a non-perpendicular angle. The second staple driver may be actuated into an angled stamped recess.

18 Claims, 12 Drawing Sheets

(56) References Cited

U.S. PATENT DOCUMENTS

| | | | |
|---|---|---|---|
| 3,496,940 | A | 2/1970 | Steinman |
| 3,526,228 | A | 9/1970 | Lyng |
| 4,222,383 | A | 9/1980 | Schossow |
| 4,513,746 | A | 4/1985 | Aranyi et al. |
| 4,549,545 | A | 10/1985 | Levy |
| 4,610,250 | A | 9/1986 | Green |
| 4,693,720 | A | 9/1987 | Scharnberg et al. |
| 4,805,823 | A | 2/1989 | Rothfuss |
| 5,011,493 | A | 4/1991 | Belykh et al. |
| 5,064,057 | A | 11/1991 | Iwatsuki et al. |
| 5,263,629 | A | 11/1993 | Trumbull et al. |
| 5,282,829 | A | 2/1994 | Hermes |
| 5,297,324 | A | 3/1994 | Su |
| 5,327,914 | A | 7/1994 | Shlain |
| 5,366,480 | A | 11/1994 | Corriveau et al. |
| 5,383,904 | A | 1/1995 | Totakura et al. |
| 5,393,594 | A | 2/1995 | Koyfman et al. |
| 5,411,193 | A | 5/1995 | Culp |
| 5,415,334 | A | 5/1995 | Williamson, IV et al. |
| 5,465,895 | A | 11/1995 | Knodel et al. |
| 5,466,462 | A | 11/1995 | Rosenthal et al. |
| 5,496,603 | A | 3/1996 | Riedel et al. |
| 5,503,638 | A | 4/1996 | Cooper et al. |
| 5,540,375 | A | 7/1996 | Bolanos et al. |
| 5,542,594 | A | 8/1996 | McKean et al. |
| 5,565,210 | A | 10/1996 | Rosenthal et al. |
| 5,597,107 | A | 1/1997 | Knodel et al. |
| 5,607,590 | A | 3/1997 | Shimizu |
| 5,607,686 | A | 3/1997 | Totakura et al. |
| 5,632,432 | A | 5/1997 | Schulze et al. |
| 5,639,851 | A | 6/1997 | Bezwada et al. |
| 5,641,566 | A | 6/1997 | Kranzler et al. |
| 5,644,002 | A | 7/1997 | Cooper et al. |
| 5,662,260 | A * | 9/1997 | Yoon .................. 227/176.1 |
| 5,673,840 | A | 10/1997 | Schulze et al. |
| 5,690,675 | A | 11/1997 | Sawyer et al. |
| 5,704,534 | A | 1/1998 | Huitema et al. |
| 5,711,958 | A | 1/1998 | Cohn et al. |
| 5,733,308 | A | 3/1998 | Daugherty et al. |
| 5,749,968 | A | 5/1998 | Melanson et al. |
| 5,752,965 | A | 5/1998 | Francis et al. |
| 5,755,778 | A | 5/1998 | Kleshinski |
| 5,766,188 | A | 6/1998 | Igaki |
| 5,769,892 | A | 6/1998 | Kingwell |
| 5,810,855 | A | 9/1998 | Rayburn et al. |
| 5,814,055 | A | 9/1998 | Knodel et al. |
| 5,814,057 | A | 9/1998 | Oi et al. |
| 5,843,096 | A | 12/1998 | Igaki et al. |
| 5,902,312 | A | 5/1999 | Frater et al. |
| 5,997,895 | A | 12/1999 | Narotam et al. |
| 6,019,791 | A | 2/2000 | Wood |
| 6,031,148 | A | 2/2000 | Hayes et al. |
| 6,099,551 | A | 8/2000 | Gabbay |
| 6,174,333 | B1 | 1/2001 | Kadiyala et al. |
| 6,203,564 | B1 | 3/2001 | Hutton et al. |
| 6,245,081 | B1 | 6/2001 | Bowman et al. |
| 6,273,897 | B1 | 8/2001 | Dalessandro et al. |
| 6,277,397 | B1 | 8/2001 | Shimizu |
| 6,312,474 | B1 | 11/2001 | Francis et al. |
| 6,325,810 | B1 | 12/2001 | Hamilton et al. |
| 6,355,699 | B1 | 3/2002 | Vyakarnam et al. |
| 6,488,197 | B1 | 12/2002 | Whitman |
| 6,495,127 | B1 | 12/2002 | Wallace et al. |
| 6,511,748 | B1 | 1/2003 | Barrows |
| 6,592,597 | B2 | 7/2003 | Grant et al. |
| 6,638,285 | B2 | 10/2003 | Gabbay |
| 6,656,193 | B2 | 12/2003 | Grant et al. |
| 6,704,210 | B1 | 3/2004 | Myers |
| 6,783,524 | B2 | 8/2004 | Anderson et al. |
| 6,814,741 | B2 | 11/2004 | Bowman et al. |
| 6,835,336 | B2 | 12/2004 | Watt |
| 6,921,412 | B1 | 7/2005 | Black et al. |
| 6,962,594 | B1 | 11/2005 | Thevenet |
| 6,978,921 | B2 | 12/2005 | Shelton, IV et al. |
| 7,000,818 | B2 | 2/2006 | Shelton, IV et al. |
| 7,048,755 | B2 | 5/2006 | Bonutti et al. |
| 7,084,082 | B1 | 8/2006 | Shimizu |
| 7,143,923 | B2 | 12/2006 | Shelton, IV et al. |
| 7,147,138 | B2 | 12/2006 | Shelton, IV |
| 7,207,471 | B2 | 4/2007 | Heinrich et al. |
| 7,211,093 | B2 | 5/2007 | Sauer et al. |
| 7,268,205 | B2 | 9/2007 | Williams et al. |
| 7,303,108 | B2 | 12/2007 | Shelton, IV |
| 7,335,212 | B2 | 2/2008 | Edoga et al. |
| 7,367,485 | B2 | 5/2008 | Shelton, IV et al. |
| 7,377,928 | B2 | 5/2008 | Zubik et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,434,715 | B2 | 10/2008 | Shelton, IV et al. |
| 7,517,356 | B2 | 4/2009 | Heinrich |
| 7,607,557 | B2 | 10/2009 | Shelton, IV et al. |
| 7,635,074 | B2 | 12/2009 | Olson et al. |
| 7,721,930 | B2 | 5/2010 | McKenna et al. |
| 7,738,971 | B2 | 6/2010 | Swayze et al. |
| 7,845,533 | B2 | 12/2010 | Marczyk et al. |
| 8,070,034 | B1 * | 12/2011 | Knodel .................. 227/176.1 |
| 2002/0165559 | A1 | 11/2002 | Grant et al. |
| 2003/0120284 | A1 | 6/2003 | Palacios et al. |
| 2003/0183671 | A1 | 10/2003 | Mooradian et al. |
| 2004/0093024 | A1 | 5/2004 | Lousararian et al. |
| 2004/0167572 | A1 | 8/2004 | Roth et al. |
| 2004/0254608 | A1 | 12/2004 | Huitema et al. |
| 2005/0042250 | A1 | 2/2005 | Damien et al. |
| 2005/0059996 | A1 | 3/2005 | Bauman et al. |
| 2005/0070929 | A1 | 3/2005 | Dalessandro et al. |
| 2005/0101834 | A1 | 5/2005 | Merade |
| 2005/0107810 | A1 | 5/2005 | Morales et al. |
| 2005/0145671 | A1 | 7/2005 | Viola |
| 2005/0154403 | A1 | 7/2005 | Sauer et al. |
| 2005/0245965 | A1 | 11/2005 | Orban, III et al. |
| 2005/0249772 | A1 | 11/2005 | Malaviya et al. |
| 2005/0251153 | A1 | 11/2005 | Sakamoto et al. |
| 2005/0283256 | A1 | 12/2005 | Sommerich et al. |
| 2005/0288767 | A1 | 12/2005 | Kujawski et al. |
| 2006/0004388 | A1 | 1/2006 | Whayne et al. |
| 2006/0004407 | A1 | 1/2006 | Hiles et al. |
| 2006/0047312 | A1 | 3/2006 | Olmo et al. |
| 2006/0093655 | A1 | 5/2006 | Bar et al. |
| 2006/0094318 | A1 | 5/2006 | Matsuda et al. |
| 2006/0135992 | A1 | 6/2006 | Bettuchi et al. |
| 2006/0173470 | A1 | 8/2006 | Oray et al. |
| 2006/0212069 | A1 | 9/2006 | Shelton, IV |
| 2006/0229672 | A1 | 10/2006 | Forsberg |
| 2006/0265006 | A1 | 11/2006 | White et al. |
| 2006/0265007 | A1 | 11/2006 | White et al. |
| 2007/0016227 | A1 | 1/2007 | de la Torre et al. |
| 2007/0034667 | A1 | 2/2007 | Holsten et al. |
| 2007/0034669 | A1 | 2/2007 | de la Torre et al. |
| 2007/0049953 | A2 | 3/2007 | Shimoji et al. |
| 2007/0060932 | A1 | 3/2007 | Stack et al. |
| 2007/0066981 | A1 | 3/2007 | Meagher |
| 2007/0112360 | A1 | 5/2007 | De Deyne et al. |
| 2007/0128243 | A1 | 6/2007 | Serafica et al. |
| 2007/0131732 | A1 | 6/2007 | Holsten et al. |
| 2007/0150002 | A1 | 6/2007 | Szabo et al. |
| 2007/0156140 | A1 | 7/2007 | Baily |
| 2007/0190108 | A1 | 8/2007 | Datta et al. |
| 2007/0207180 | A1 | 9/2007 | Tanihara et al. |
| 2007/0213522 | A1 | 9/2007 | Harris et al. |
| 2007/0219571 | A1 | 9/2007 | Balbierz et al. |
| 2007/0225642 | A1 | 9/2007 | Houser et al. |
| 2007/0243227 | A1 | 10/2007 | Gertner |
| 2007/0246505 | A1 | 10/2007 | Pace-Floridia et al. |
| 2007/0286892 | A1 | 12/2007 | Herzberg et al. |
| 2008/0039871 | A1 | 2/2008 | Wallace et al. |
| 2008/0077131 | A1 | 3/2008 | Yates |
| 2008/0078800 | A1 | 4/2008 | Hess et al. |
| 2008/0078801 | A1 | 4/2008 | Shelton, IV et al. |
| 2008/0078802 | A1 | 4/2008 | Hess et al. |
| 2008/0078803 | A1 | 4/2008 | Shelton, IV et al. |
| 2008/0078804 | A1 | 4/2008 | Shelton, IV et al. |
| 2008/0078805 | A1 | 4/2008 | Omaits et al. |
| 2008/0078806 | A1 | 4/2008 | Omaits et al. |

(56) References Cited

U.S. PATENT DOCUMENTS

| | | | |
|---|---|---|---|
| 2008/0078807 A1 | 4/2008 | Hess et al. |
| 2008/0081881 A1 | 4/2008 | Swetlin et al. |
| 2008/0082124 A1 | 4/2008 | Hess et al. |
| 2008/0082126 A1 | 4/2008 | Murray et al. |
| 2008/0110959 A1 | 5/2008 | Orban, III et al. |
| 2008/0114381 A1 | 5/2008 | Voegele et al. |
| 2008/0114385 A1 | 5/2008 | Byrum et al. |
| 2008/0114399 A1 | 5/2008 | Bonutti |
| 2008/0125812 A1 | 5/2008 | Zubik et al. |
| 2008/0128469 A1 | 6/2008 | Dalessandro et al. |
| 2008/0140115 A1 | 6/2008 | Stopek |
| 2008/0200949 A1 | 8/2008 | Hiles et al. |
| 2008/0314960 A1 | 12/2008 | Marczyk et al. |
| 2009/0001122 A1 | 1/2009 | Prommersberger et al. |
| 2009/0076510 A1 | 3/2009 | Bell et al. |
| 2009/0118747 A1 | 5/2009 | Bettuchi et al. |
| 2010/0127042 A1* | 5/2010 | Shelton, IV ............ 227/176.1 |
| 2013/0032626 A1 | 2/2013 | Smith et al. |
| 2013/0037596 A1 | 2/2013 | Bear et al. |
| 2013/0041406 A1 | 2/2013 | Bear et al. |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068820 A1 | 3/2013 | Miller et al. |
| 2013/0075446 A1 | 3/2013 | Wang et al. |
| 2013/0075447 A1 | 3/2013 | Weisenburgh et al. |
| 2013/0075451 A1 | 3/2013 | Balek et al. |
| 2013/0082086 A1 | 4/2013 | Hueil et al. |

FOREIGN PATENT DOCUMENTS

| | | | |
|---|---|---|---|
| EP | 328 401 | 8/1989 | |
| EP | 00641546 A1 * | 2/1994 | ........... A61B 17/064 |
| EP | 0 641 546 | 3/1995 | |
| EP | 0 667 119 | 8/1995 | |
| EP | 0 781 564 | 7/1997 | |
| EP | 0 818 470 | 1/1998 | |
| EP | 1 098 024 | 5/2001 | |
| EP | 1 229 841 | 8/2002 | |
| EP | 1 494 596 | 1/2005 | |
| EP | 1 621 141 | 2/2006 | |
| EP | 1 647 286 | 4/2006 | |
| EP | 1 759 640 | 3/2007 | |
| EP | 1 836 974 | 9/2007 | |
| EP | 2 165 652 | 3/2010 | |
| FR | 2 789 885 | 8/2000 | |
| FR | 2 850 281 | 7/2004 | |
| GB | 222 954 | 10/1924 | |
| GB | 493 459 | 10/1938 | |
| GB | 913 218 | 12/1962 | |
| JP | 107 2740 | 3/1989 | |
| JP | 3146773 | 6/1991 | |
| JP | 5076586 | 3/1993 | |
| JP | 11309151 | 11/1999 | |
| WO | WO 93/10731 | 6/1993 | |
| WO | WO 98/38923 | 9/1998 | |
| WO | WO 01/17446 | 3/2001 | |
| WO | WO 02/09593 | 2/2002 | |
| WO | WO 02/22184 | 3/2002 | |
| WO | WO 03/094743 | 11/2003 | |
| WO | WO 2004/060425 | 7/2004 | |
| WO | WO 2006/081174 | 8/2006 | |
| WO | WO 2006/106269 | 10/2006 | |
| WO | WO 2007/067621 | 6/2007 | |
| WO | WO 2008/057281 | 5/2008 | |

OTHER PUBLICATIONS

Abstract for FR2789885.
Abstract for FR2850281.
Abstract for JP1072740.
Abstract for JP11309151.
Abstract for JP3146773.
Abstract for JP5076586.

* cited by examiner

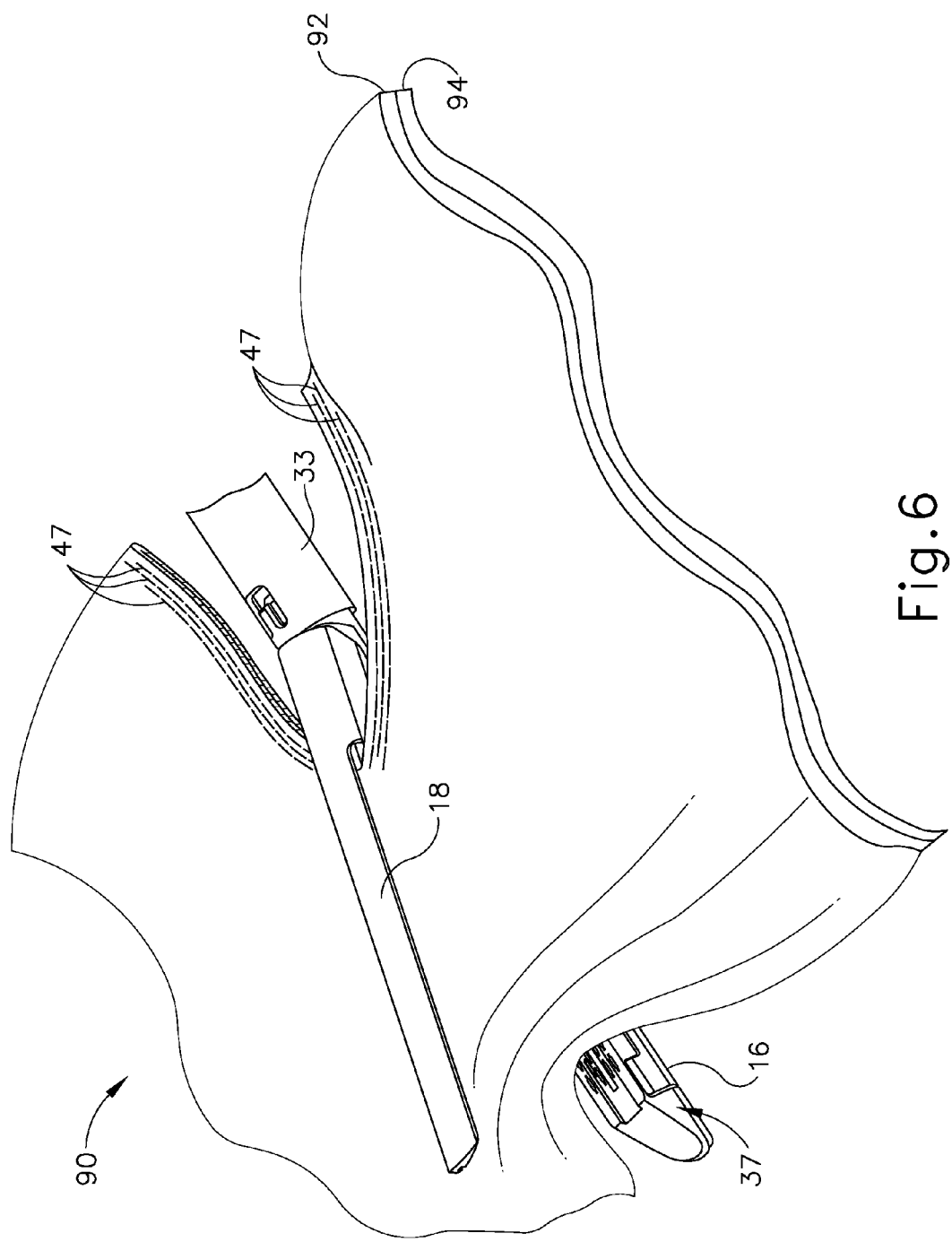

DUAL STAPLE CARTRIDGE FOR SURGICAL STAPLER

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 6 depicts a perspective view of the end effector of FIG. 2, positioned at tissue and having been actuated once in the tissue;

Figure 1A:
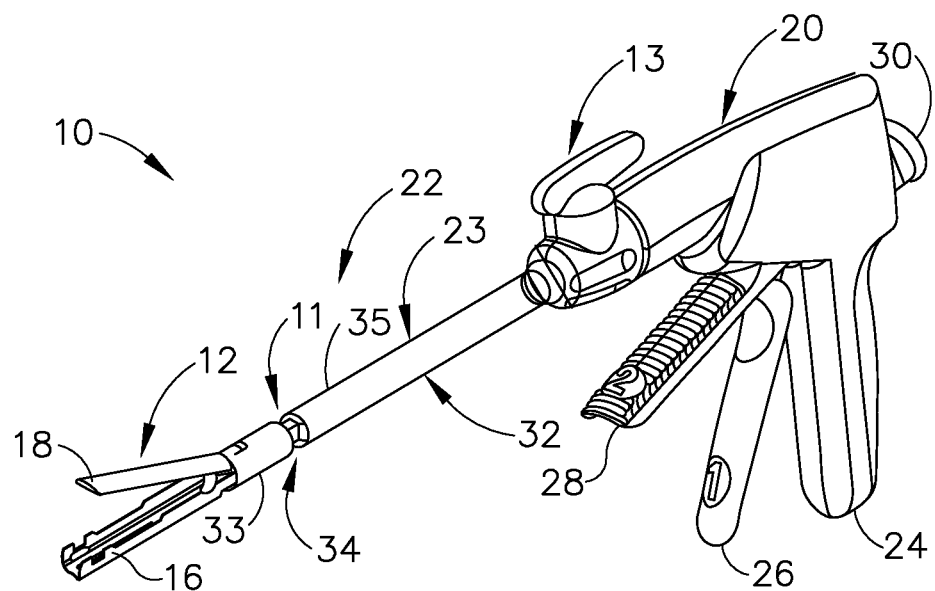
FIG. 1A depicts a perspective view of an articulating surgical instrument with an end effector in a nonarticulated position.
Figure 1B:
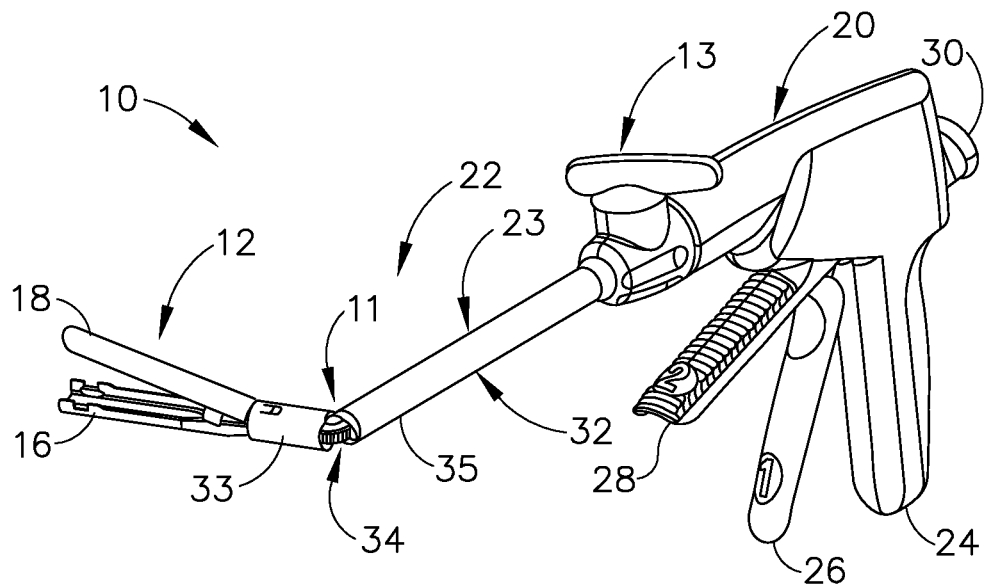
FIG. 1B depicts a perspective view of the surgical instrument of FIG. 1A with an end effector in an articulated position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical stapling and severing instrument (10) includes handle portion (20) connected to implement portion (22), the latter further comprising shaft (23) distally terminating in an articulation mechanism (11) and a distally attached end effector (12). Once articulation mechanism (11) and end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal closure ring (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
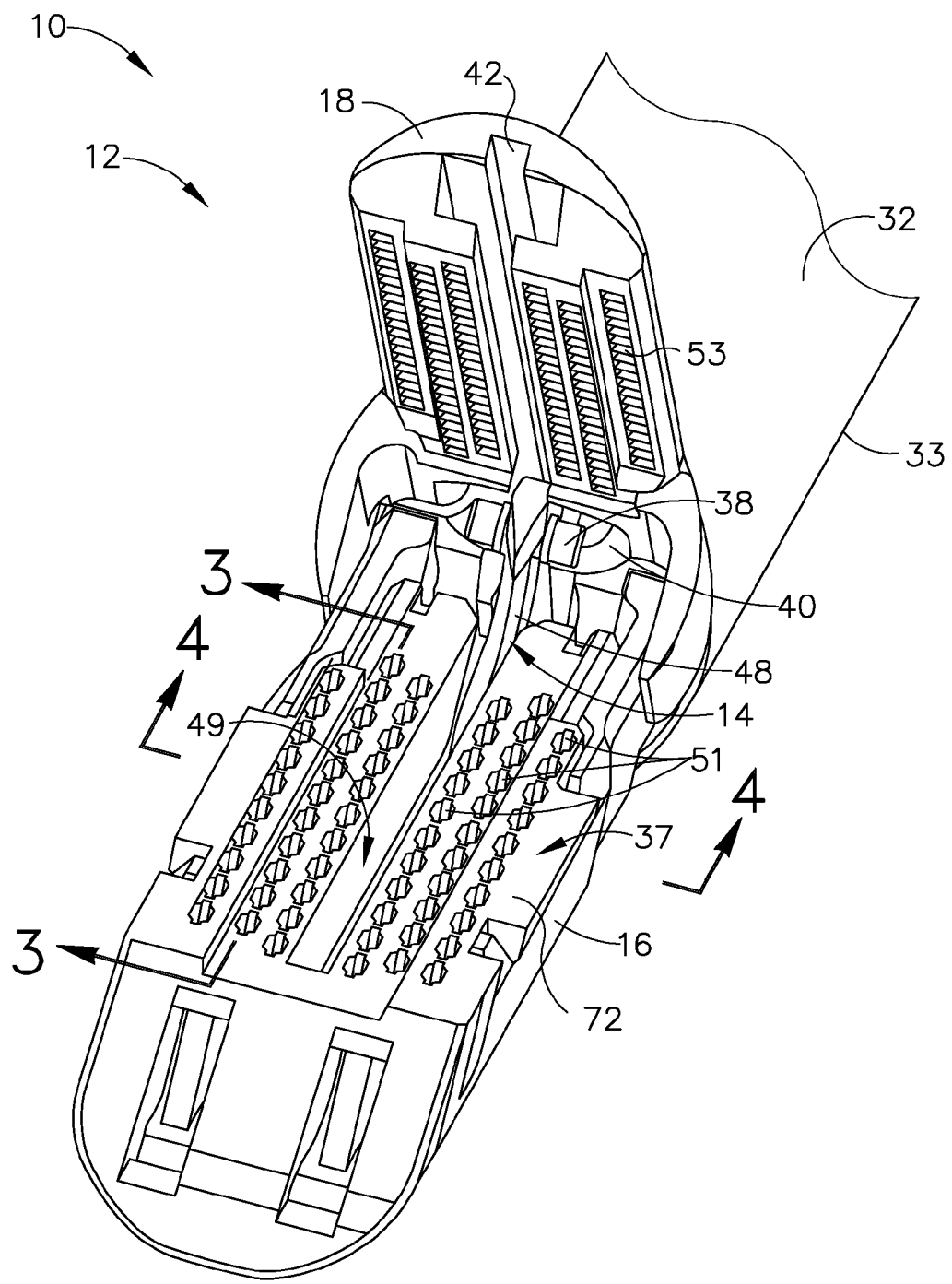
FIG. 2 depicts a perspective view of an opened end effector of the surgical instrument of FIGS. 1A-1B.
Figure 3A:
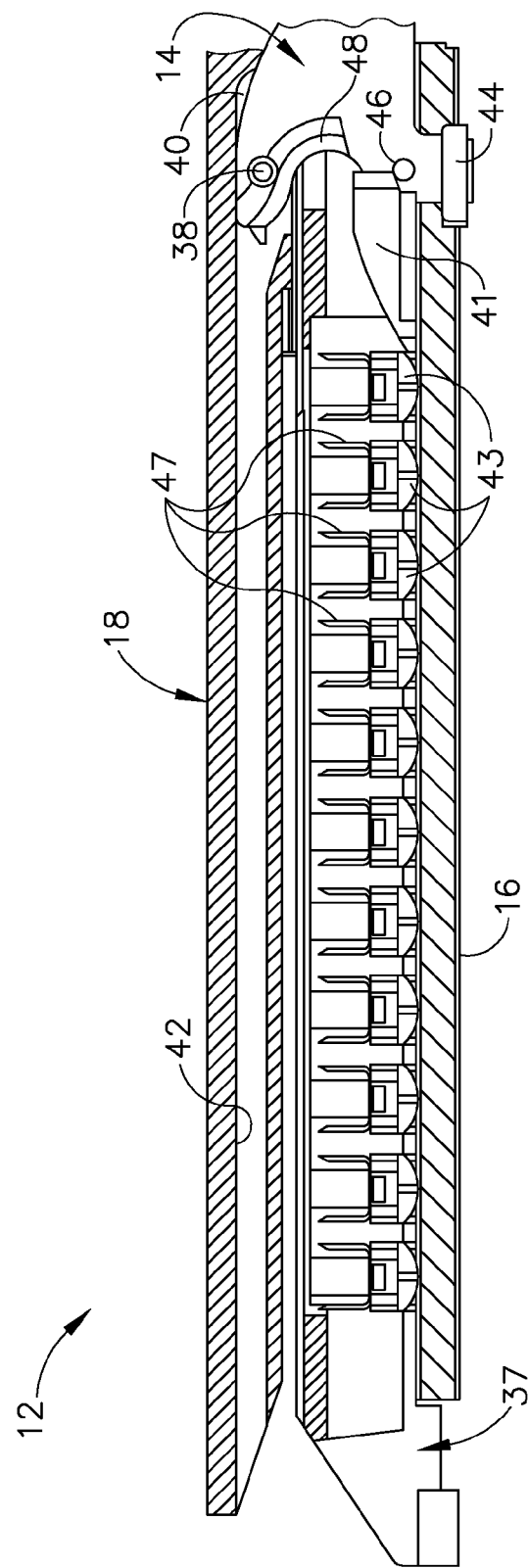
FIG. 3A depicts a side cross-sectional view of the end effector of FIG. 2, taken along line 3-3 of FIG. 2, with the firing bar in a proximal position.
Figure 3B:
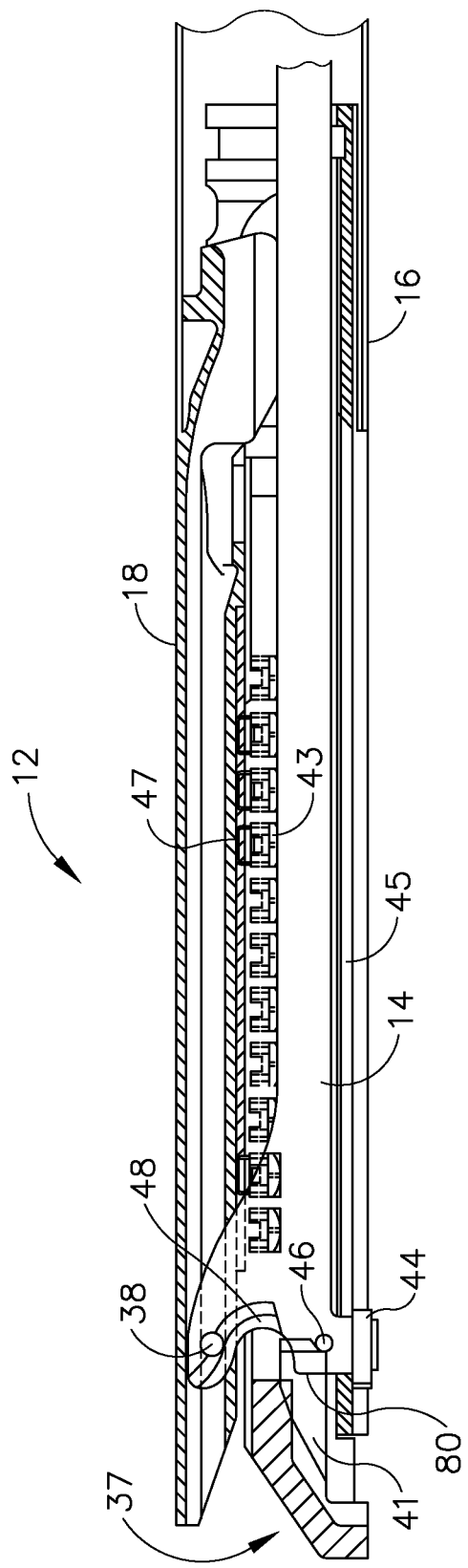
FIG. 3B depicts a side cross-sectional view of the end effector of FIG. 2, taken along line 3-3 of FIG. 2, but showing the firing bar in a distal position.
Figure 4:
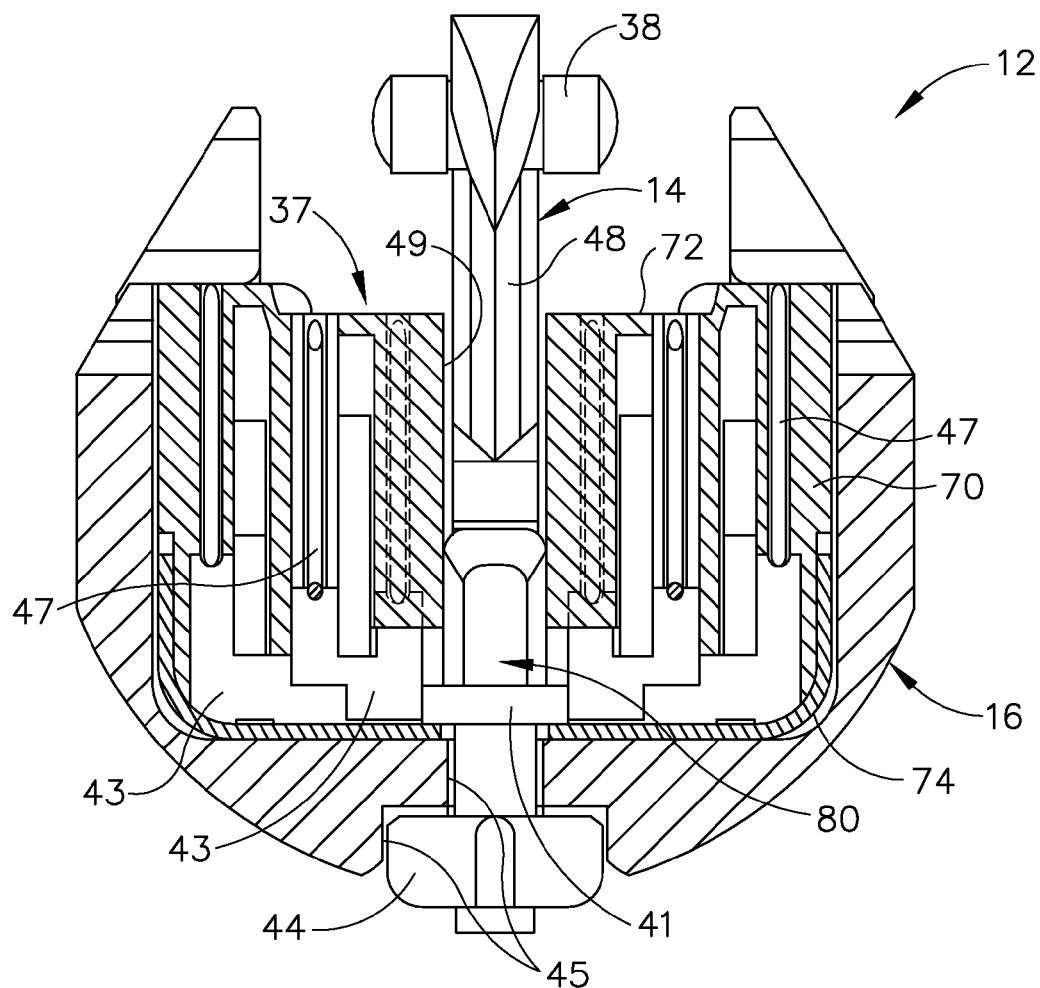
FIG. 4 depicts an end cross-sectional view of the end effector of FIG. 2, taken along line 4-4 of FIG. 2.
Figure 5:
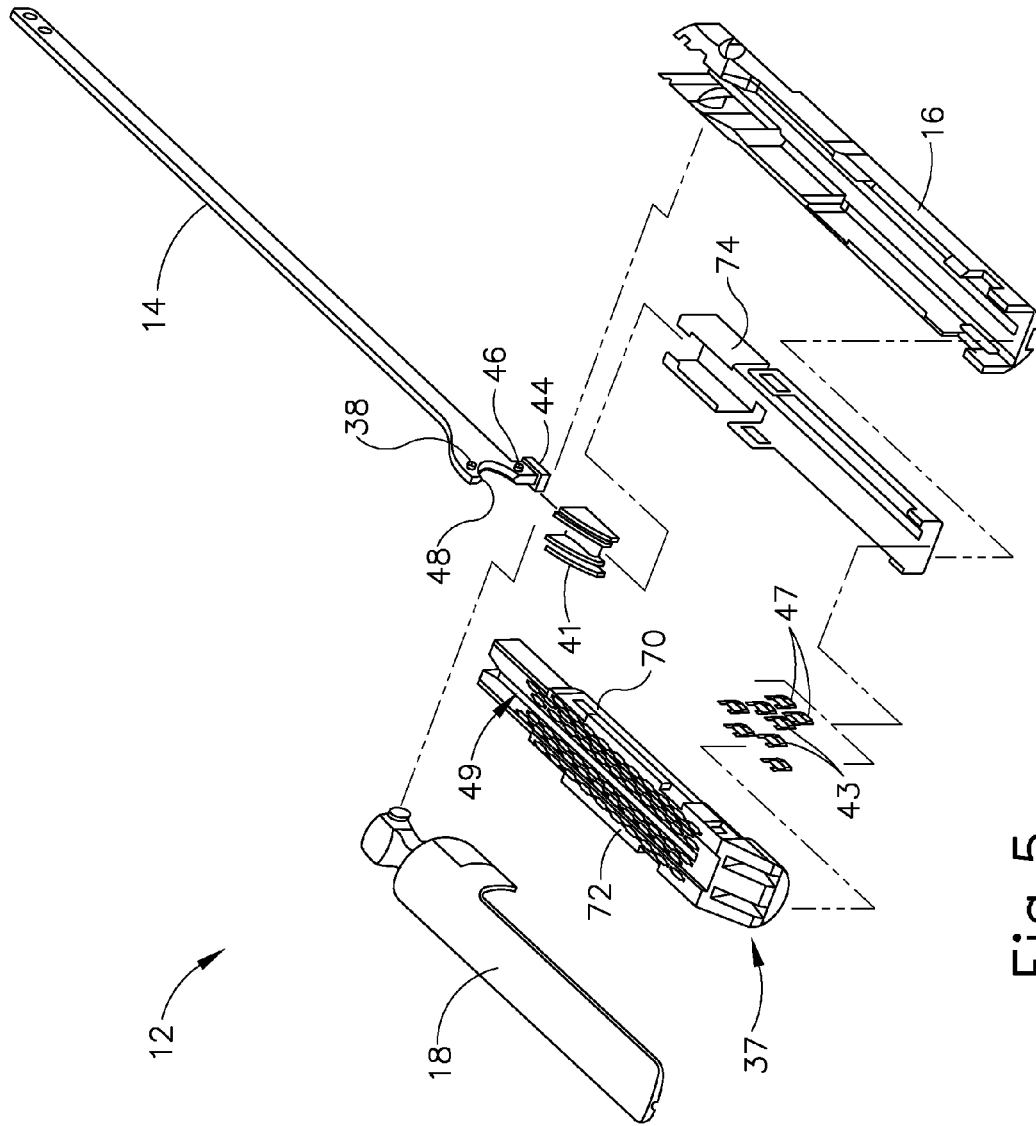
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (72) on one side of vertical slot (49), with another set of three rows of staple apertures (51) being formed through upper deck (72) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into slot (49) within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

FIG. 6 shows end effector (12) having been actuated through a single stroke through tissue (90). Cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; and/or U.S. Pat. No. 7,721,930.

As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Dual Staple Cartridges

In some instances it may be useful to utilize dual staple cartridges (37). For instance, it may be useful to have a bottom staple cartridge (37) and a top staple cartridge (37) inserted into end effector (12) to staple tissue (90) from an opposing direction. In addition, the use of opposing staples may further promote secure coupling of material to both sides of tissue (90). In some instances, it may also be useful to angle staples (47). Such angled staples (47) may permit the vertical dimension of staple cartridges (37) to be reduced. While the following describes merely illustrative examples of dual staple cartridge configurations, other suitable configurations will be apparent to those of ordinary skill in the art in view of the teachings herein.

A. Exemplary Rotatable Staple Driver Dual Staple Cartridges

Figure 7A:
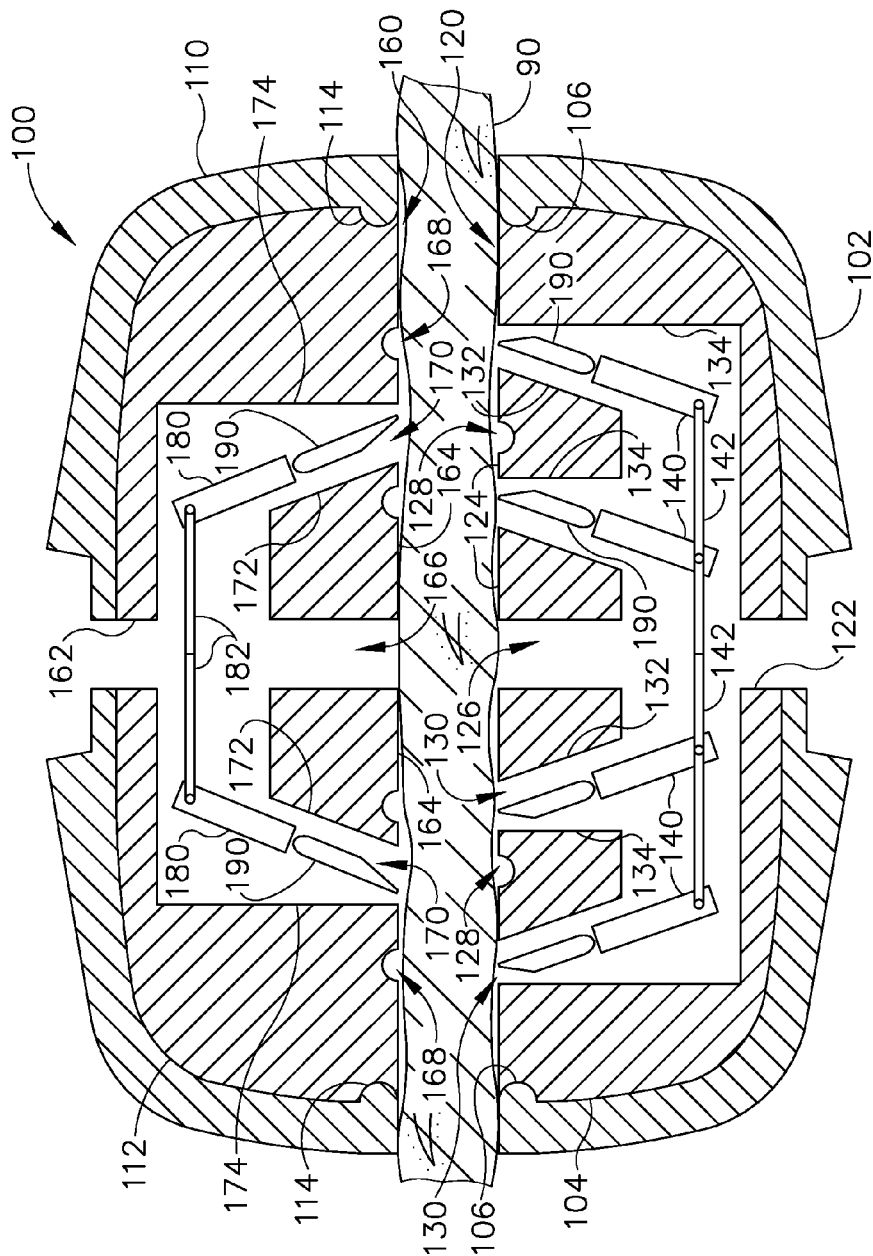
FIG. 7A depicts a front elevation cross-sectional view of an exemplary end effector having an exemplary lower cartridge and upper cartridge.
Figure 7B:
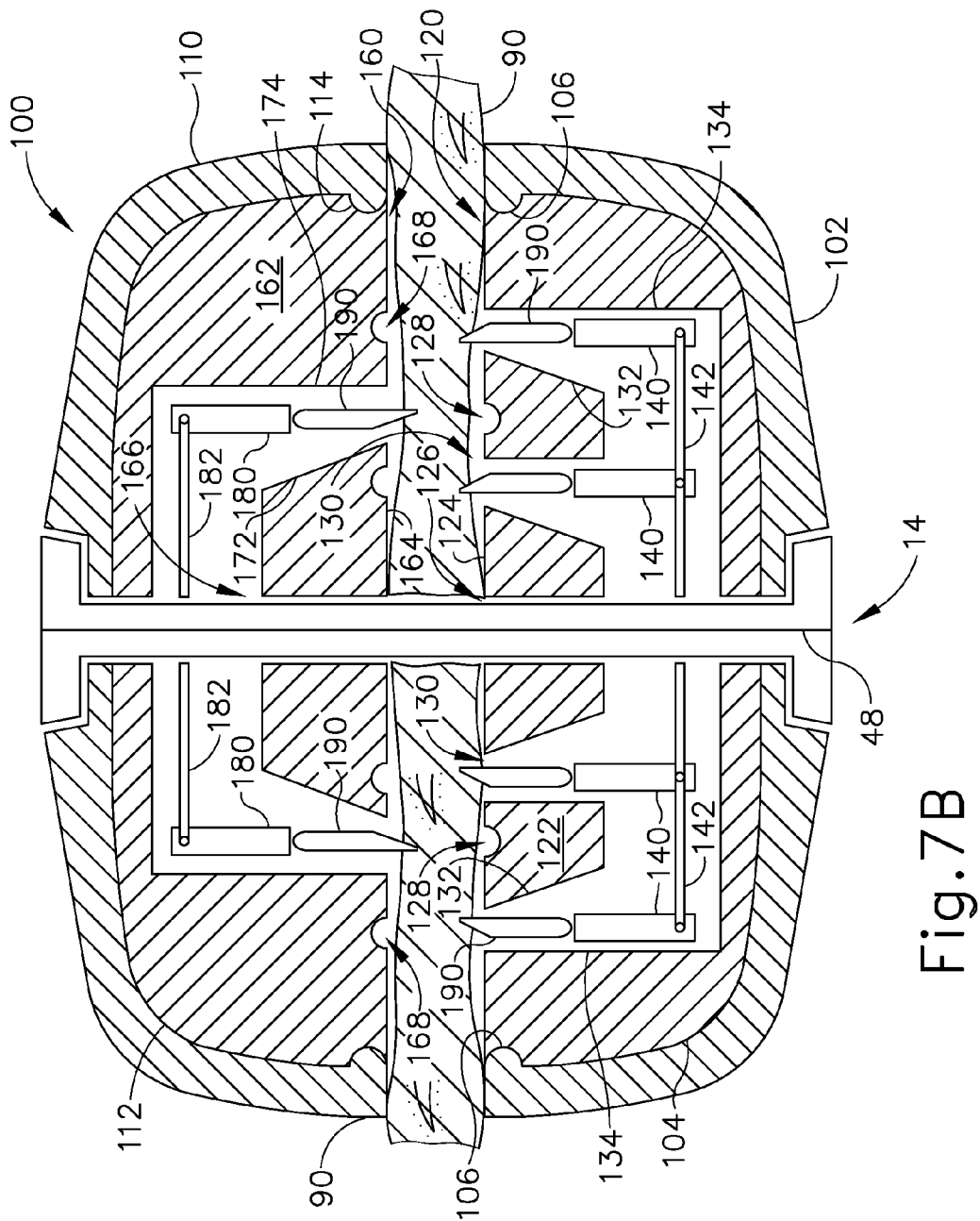
FIG. 7B depicts a front elevation cross-sectional view of the end effector of FIG. 7A, showing the firing bar extending through a vertical slot in the lower cartridge and the upper cartridge.
Figure 7C:
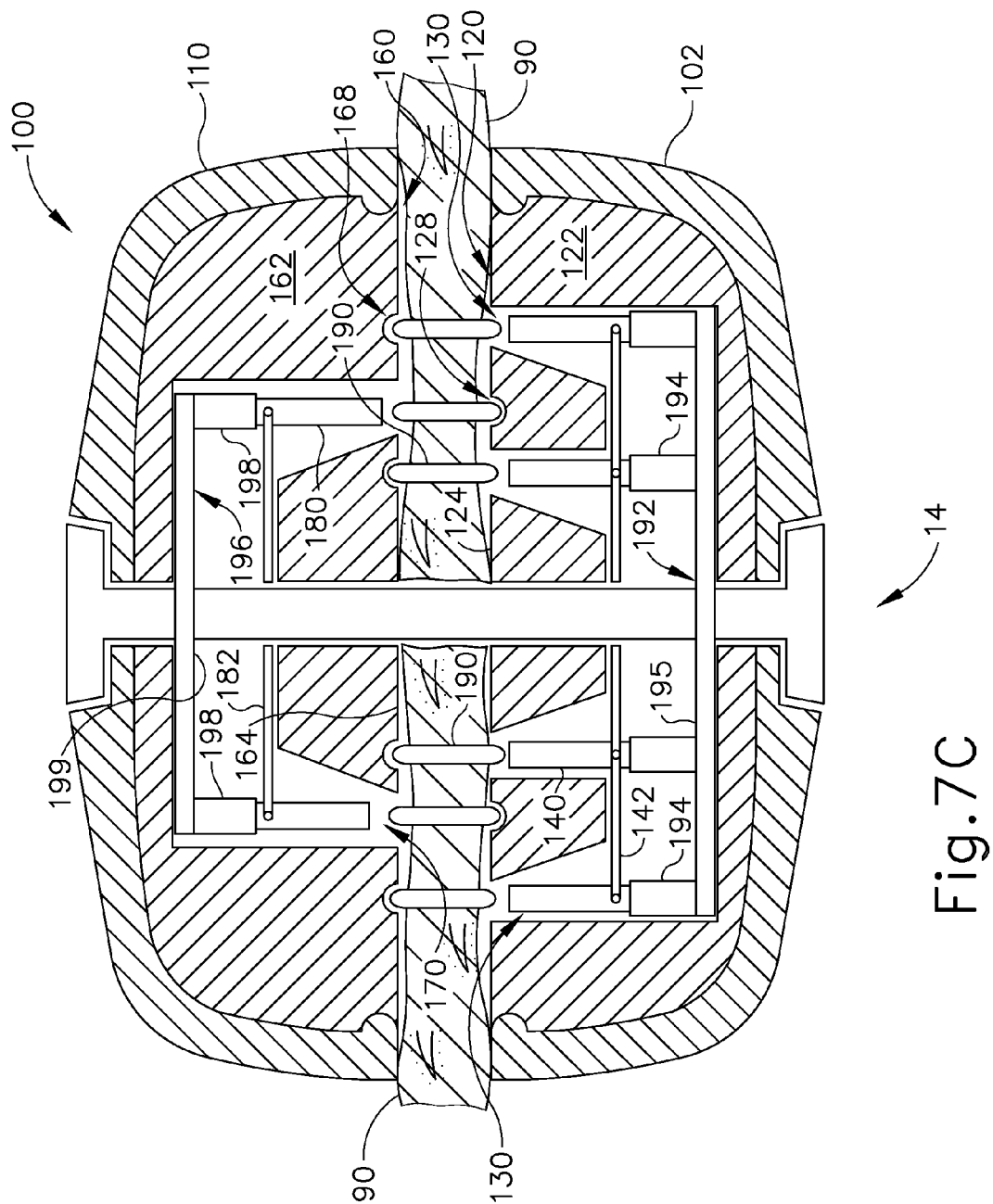
FIG. 7C depicts a front elevation cross-sectional view of the end effector of FIG. 7A, showing an exemplary upper wedge sled and lower wedge sled camming the staple drivers.

FIGS. 7A-7C depict an exemplary end effector (100) configured to receive a lower cartridge (120) and an upper cartridge (160). It should be understood that instrument (10) may be readily modified to incorporate end effector (100). In the present example, end effector (100) includes a lower jaw (102) and a pivotable upper jaw (110). End effector (100) is coupled to handle portion (20), described above. In particular, a clinician may pivotally draw closure trigger (26) toward pistol grip (24) to cause clamping, or closing, of the upper jaw (110) toward lower jaw (102) of end effector (100). In the present example, lower jaw (102) defines a lower recess (104) configured to receive lower cartridge (120). In some versions lower jaw (102) further includes detents (106) or snap features that are configured to selectively couple lower cartridge (120) to lower jaw (102). In addition or in the alternative, lower jaw (102) may include an open distal end and longitudinal rails (not shown) onto or below which lower cartridge (120) may be slid. Lower jaw (102) and/or lower cartridge (120) may include detents or snap features at a distal end to selectively couple lower cartridge (120) to lower jaw (102) when lower cartridge (120) is slid proximally along the longitudinal rails. Of course other configurations for inserting and coupling lower cartridge (120) to lower jaw (102) will be apparent to one of ordinary skill in the art in view of the teachings herein.

Upper jaw (110) defines an upper recess (112) configured to receive upper cartridge (160). In some versions upper jaw (110) further includes detents (114) or snap features that are configured to selectively couple upper cartridge (160) to upper jaw (110). In addition or in the alternative, upper jaw (110) may include an open distal end and longitudinal rails (not shown) onto or above which upper cartridge (160) may be slid. Upper jaw (110) and/or upper cartridge (160) may include detents or snap features at a distal end to selectively couple upper cartridge (160) to upper jaw (110) when upper cartridge (160) is slid proximally along the longitudinal rails. Of course other configurations for inserting and coupling upper cartridge (160) to upper jaw (110) will be apparent to one of ordinary skill in the art in view of the teachings herein.

Lower cartridge (120) of the present example comprises a cartridge body (122), an upper deck (124), a plurality of staple apertures (130), a plurality of staple drivers (140), and a vertical slot (126). Lower cartridge (120) may be further constructed in accordance with at least some of the teachings of cartridges (37, 160, 220, 260) described herein. As shown in FIG. 7A, upper deck (124) includes vertical slot (126) formed along a longitudinal axis of lower cartridge (120) and four staple apertures (130) formed therein—two staple apertures (130) formed on each side of vertical slot (126). It should be understood that the four staple apertures (130) are a part of four rows of staple apertures (130) extending longitudinally along lower cartridge (120). Moreover, any number of rows of staple apertures (130) may be formed in upper deck (124), and the four rows of staple apertures (130) are merely exemplary. In addition, staple apertures (130) may be disposed about vertical slot (126) in a variety of configurations. For instance, staple apertures (130) may be symmetrically disposed about vertical slot (126) or staple apertures (130) may be asymmetrically disposed about vertical slot (126). By way of example only, for a curved end effector (100), three staple apertures (130) may be disposed on one side of vertical slot (126) and a single staple aperture (130) may be disposed on the opposing side.

Upper deck (124) of the present example further comprises staple forming pockets (128) into which staples (190) are cammed via staple drivers (180) of upper cartridge (160), as will be described in more detail below. In the present example, each staple aperture (130) is further defined by an angled interior wall (132) and a vertical exterior wall (134). Alternatively, walls (132, 134) may include arcuate walls. Of course other configurations and orientations for staple apertures (130) will be apparent to one of ordinary skill in the art in view of the teachings herein. Vertical slot (126) extends longitudinally through upper deck (124) and cartridge body (122) such that firing bar (14) is actuatable therethrough. In some versions vertical slot (126) is a longitudinally straight slot while in other versions vertical slot (126) may be curved along the longitudinal axis for a curved end effector (100).

Staple drivers (140) of the present example are disposed within cartridge body (122) and are vertically movable members within lower cartridge (120). In some versions staple drivers (140) are selectively coupled within cartridge body (122) such that staple drivers (140) are prevented from inadvertently actuating relative to cartridge body (122) until a lower wedge sled (192), described below, engages staple drivers (140). For instance, staple drivers (140) may be adhesively attached to cartridge body (122). In other versions, staple drivers (140) may each include a tab (not shown) that is insertable into a slot (not shown) formed in cartridge body (122) such that an interference fit or detent fit is formed. Accordingly, staple drivers (140) are selectively secured relative to cartridge body (122) even if the user rotates or inverts end effector (100). Of course other selectively coupleable configurations will be apparent to one of ordinary skill in the art in view of the teachings herein.

In the present example, a plurality of staples (190) are also disposed within cartridge body (122) and are disposed above corresponding staple drivers (140). In particular, each staple (190) is driven vertically within cartridge body (122) by a respective staple driver (140) to drive staple (190) out through an associated staple aperture (130). In some versions staples (190) are selectively coupled to staple drivers (140) such that staples (190) are prevented from inadvertently actuating relative to staple drivers (140) until lower wedge sled (192), described below, engages staple drivers (140) to expel staples (190) out of staple apertures (130). For instance, staples (190) may be adhesively attached to staple drivers (140). In other versions, staples (190) may each include a tab (not shown) that is insertable into a slot (not shown) formed in staple drivers (140) such that an interference fit is formed. Further still, a snap feature may be included on staple drivers (140) to retain staple (190) with staple driver (140) until deployed. In some versions, staple drivers (140) may include a release tab (not shown) that engages a tab (not shown) on cartridge body (122) to release staple (190) as staple drivers (140) are actuated vertically. Such a tab on cartridge body (122) may be at or near upper deck (124) such that staples (190) are released only when staple driver (140) is at its vertical actuation peak. Accordingly, staples (190) are selectively secured relative to staple drivers (140) even if the user rotates or inverts end effector (100). In addition to or in lieu of being secured to staple drivers (140), staples (190) may be selectively secured to cartridge body (122), such as by an interference fit and/or otherwise through friction.

In the present example, staple drivers (140) further comprise an actuation member (142) pivotally coupled to one or more staple drivers (140) and operable to move staple drivers (140) relative to cartridge body (122). As shown in FIG. 7A, each actuation member (142) comprises a rod that is pivotally coupled to two staple drivers (140). In the present example, a first actuation member (142) is pivotally coupled to a first set of two staple drivers (140) on a first side of vertical slot (126).

A second actuation member (142) is pivotally coupled to a second set of two staple drivers (140) on the opposing side of vertical slot (126). As will be discussed in more detail herein, actuation members (142) are configured to be cammed outwardly relative to cartridge body (122) by firing bar (14) such that staple drivers (140) pivot from a first position, in which staple drivers (140) are at an angle relative to upper deck (124), to a second position, in which staple drivers (140) are substantially perpendicular relative to upper deck (124). Accordingly, the vertical dimension of lower cartridge (120) may be reduced. In addition, longer staples (190) may be included in lower cartridge (120) due to the initial angling of staples (190). In other words, cartridge (120) may accommodate relatively larger staples (190) than cartridge (37), without having to increase the outer diameter of end effector (100). Furthermore, lower jaw (102) and upper jaw (110) may be sized to permit more tissue (90) therebetween due to the reduced lower cartridge (120) size. Of course other configurations for staple drivers (140) and/or actuation members (142) will be apparent to one of ordinary skill in the art in view of the teachings herein. It should also be understood that staples (190) may be initially oriented at an oblique angle, like staples (190) of this example or otherwise, even in versions where anvil (18) is used instead of upper cartridge (160).

Upper cartridge (160) of the present example comprises a cartridge body (162), a lower deck (164), a plurality of staple apertures (170), a plurality of staple drivers (180), and a vertical slot (166). Upper cartridge (160) may be further constructed in accordance with at least some of the teachings of cartridges (37, 120, 220, 260) described herein. As shown in FIG. 7A, lower deck (164) includes vertical slot (166) formed along a longitudinal axis of upper cartridge (160) and a pair of staple apertures (170) formed therein—one staple aperture (170) formed on each side of vertical slot (166). It should be understood that the two staple apertures (170) are a part of two rows of staple apertures (130) extending longitudinally along upper cartridge (160). Moreover, any number of rows of staple apertures (170) may be formed in lower deck (164), and the two rows of staple apertures (170) are merely exemplary. In addition, staple apertures (170) may be disposed about vertical slot (166) in a variety of configurations. For instance, staple apertures (170) may be symmetrically disposed about vertical slot (166) or staple apertures (170) may be asymmetrically disposed about vertical slot (166). By way of example only, for a curved end effector (100), both staple apertures (170) may be disposed on the same side of vertical slot (166).

Lower deck (164) further comprises staple forming pockets (168) into which staples (190) are cammed via staple drivers (140) of lower cartridge (120), described below. In the present example, each staple aperture (170) is further defined by an angled interior wall (172) and a vertical exterior wall (174). Alternatively, walls (172, 174) may include arcuate walls. Of course other configurations and orientations for staple apertures (170) will be apparent to one of ordinary skill in the art in view of the teachings herein. Vertical slot (166) extends longitudinally through lower deck (164) and cartridge body (162) such that firing bar (14) is actuatable therethrough. In some versions vertical slot (166) is a longitudinally straight slot while in other versions vertical slot (166) may be curved along the longitudinal axis for a curved end effector (100).

Staple drivers (180) of the present example are disposed within cartridge body (162) and are vertically movable members within upper cartridge (160). In some versions staple drivers (180) are selectively coupled within cartridge body (162) such that staple drivers (180) are prevented from actuating relative to cartridge body (162) until an upper wedge sled (196), described below, engages staple drivers (180). For instance, staple drivers (180) may be adhesively attached to cartridge body (162). In other versions, staple drivers (180) may each include a tab (not shown) that is insertable into a slot (not shown) formed in cartridge body (162) such that an interference fit or detent fit is formed. Accordingly, staple drivers (180) are selectively secured relative to cartridge body (162) such that staple drivers (180) do not move due to the force of gravity. Of course other selectively coupleable configurations will be apparent to one of ordinary skill in the art in view of the teachings herein.

In the present example, a plurality of staples (190) are also disposed within cartridge body (162) and are disposed below corresponding staple drivers (180), as shown in FIG. 7A. In particular, each staple (190) is driven vertically within cartridge body (162) by a respective staple driver (180) to drive staple (190) out through an associated staple aperture (170). In some versions staples (190) are selectively coupled to staple drivers (180) such that staples (190) are prevented from inadvertently actuating relative to staple drivers (180) until upper wedge sled (196), described below, engages staple drivers (180) to expel staples (190) out of staple apertures (170). For instance, staples (190) may be adhesively attached to staple drivers (180). In other versions, staples (190) may each include a tab (not shown) that is insertable into a slot (not shown) formed in staple drivers (180) such that an interference fit is formed. Further still, a snap feature may be included on staple drivers (180) to retain staple (190) with staple driver (180) until deployed. In some versions, staple drivers (180) may include a release tab (not shown) that engages a tab (not shown) on cartridge body (162) to release staple (190) as staple drivers (180) are actuated. Such a tab on cartridge body (162) may be at or near lower deck (164) such that staples (190) are released only when staple driver (180) is at the end of its actuation movement. Accordingly, staples (190) are selectively secured relative to staple drivers (180) such that staples (190) do not disengage from staple drivers (180) due to the force of gravity. In addition to or in lieu of being secured to staple drivers (180), staples (190) may be selectively secured to cartridge body (162), such as by an interference fit and/or otherwise through friction.

In the present example, staple drivers (180) further comprise an actuation member (182) pivotally coupled to one or more staple drivers (180) and operable to move staple drivers (180) relative to cartridge body (162). As shown in FIG. 7A, each actuation member (182) comprises a rod that is pivotally coupled to a staple driver (180). In the present example, a first actuation member (182) is pivotally coupled to a first staple driver (180) on a first side of vertical slot (166). A second actuation member (182) is pivotally coupled to a second staple driver (180) on the opposing side of vertical slot (166). As will be discussed in more detail herein, actuation members (182) are configured to be cammed outwardly relative to cartridge body (162) by firing bar (14) such that staple drivers (180) pivot from a first position, in which staple drivers (180) are at an angle relative to lower deck (164), to a second position, in which staple drivers (180) are substantially perpendicular relative to upper deck (164). Accordingly, the vertical dimension of upper cartridge (160) may be reduced. In addition, longer staples (190) may be included in upper cartridge (160) due to the initial angling of staples (190). In other words, cartridge (160) may accommodate relatively larger staples (190) than cartridge (37), without having to increase the outer diameter of end effector (100). Furthermore, lower jaw (102) and upper jaw (110) may be sized to permit more tissue (90) therebetween due to the reduced upper cartridge (160) size. Of course other configurations for staple drivers (180) and/or actuation members (182) will be apparent to one of ordinary skill in the art in view of the teachings herein.

FIGS. 7A-7C depict the firing of firing bar (14) through lower and upper cartridges (120, 160) to deploy staples (190) into tissue (90). As shown in FIG. 7A, tissue (90) is secured between lower jaw (102) and upper jaw (110) after closure trigger (26) has been actuated. In this initial position, actuation members (142, 182) have not been engaged by firing bar (14), so staple drivers (140, 180) are at an angle relative to cartridge bodies (122, 162), respectively. As discussed previously, frame (34) longitudinally slidingly supports a firing drive member that extends through shaft (23) and communicates a firing motion from firing trigger (28) to firing bar (14), as shown in FIGS. 1-5. When firing trigger (28) is actuated by a user, firing bar (14) advances distally relative to handle portion (20). As shown in FIG. 7B, cutting edge (48) of firing bar (14) advances distally to simultaneously sever tissue (90) and cam actuation members (142, 182) outwardly relative to firing bar (14). As a result, staple drivers (140, 180) are pivoted by actuation members (142, 182) and walls (134, 174) such that staple drivers (140, 180) are substantially vertical relative to upper and lower decks (124, 164). As also shown in FIG. 7B, firing bar (14) includes a pair of flanges on the top and bottom ends of firing bar (14) that slide along exterior channels of the lower and upper jaws (102, 110). As will be apparent to one of ordinary skill in the art, the flanges cooperatively compress bottom and upper jaws (102, 110) together to further secure tissue (90) therebetween as firing bar (14) is actuated distally.

With staple drivers (140, 180) in a substantially vertical orientation, as shown in FIG. 7C, a lower wedge sled (192) and an upper wedge sled (196) are advanced distally through lower cartridge (120) and upper cartridge (160), respectively. Lower wedge sled (192) of the present example comprises four ramped members (194) coupled to a base member (195). Ramped members (194) are configured to cam staple drivers (140) vertically relative to upper deck (124). Of course, as with staple apertures (130), lower wedge sled (192) may have less than four or more than four ramped members (194). Upper wedge sled (196) of the present example comprises two ramped members (198) coupled to a base member (199). Ramped members (198) are configured to cam staple drivers (180) vertically relative to lower deck (164). Of course, as with staple apertures (170), upper wedge sled (196) may have less than two or more than two ramped members (198). When lower wedge sled (192) is advanced distally, staple drivers (140) are cammed vertically such that staples (190), carried by staple drivers (140), are driven out of staple apertures (130) of lower cartridge (120). Staples (190) pierce through tissue (90) and engage staple forming pockets (168) formed in lower deck (164) of upper cartridge (160). Accordingly, staples (190) are bent and staple tissue (90). Similarly, when upper wedge sled (196) is advanced distally, staple drivers (180) are cammed vertically such that staples (190), carried by staple drivers (180), are driven out of staple apertures (170) of upper cartridge (160). Staples (190) pierce through tissue (90) and engage staple forming pockets (128) formed in upper deck (124) of lower cartridge (120). Accordingly, staples (190) are bent and staple tissue (90). As shown in FIG. 7C, oppositely oriented staples (190) are stapled through tissue (90) using the present end effector (100) having a lower and upper cartridge (120, 160). The user may then release firing trigger (28) and closure trigger (26) to release the stapled tissue (90). The user may then replace lower and upper cartridges (120, 160) with new lower and upper cartridges (120, 160) to staple a new section of tissue (90).

Of course other configurations for end effector (100), lower cartridge (120) and/or upper cartridge (160) will be apparent to one of ordinary skill in the art in view of the teachings herein. For instance, in some versions a buttress material (not shown) may be coupled to lower cartridge (120) and/or upper cartridge (160). Merely exemplary configurations for lower cartridge (120) and/or upper cartridge (160) having a buttress material are disclosed in U.S. patent application Ser. No. 13/233,664, entitled "Surgical Instrument and Buttress Material, filed Sep. 15, 2011, and published Mar. 21, 2013 as U.S. Pat. Pub. No. 2013/0068816; U.S. patent application Ser. No. 13/231,064, entitled "Surgical Staple Cartridge with Self-Dispensing Staple Buttress," filed Sep. 13, 2011, and published Mar. 14, 2013 as U.S. Pat. Pub. No. 2013/0062394; U.S. patent application Ser. No. 13/232,401, entitled "Surgical Instrument with Fluid Fillable Buttress," filed Sep. 14, 2011, and published Mar. 14, 2013 as U.S. Pat. Pub. No. 2013/0062391; and U.S. patent application Ser. No. 13/251,682, entitled "Attachment of Surgical Staple Buttress to Cartridge," filed Oct. 3, 2011, published Apr. 4, 2013 as U.S. Pat. Pub. No. 2013/0082086, and issued on Dec. 2, 2014 as U.S. Pat. No. 8,899,464, the disclosures of which are incorporated by reference herein.

In addition, or in some versions in the alternative, an adjunct material (e.g., an adhesive, a therapeutic agent, etc.) may be applied to tissue (90) via lower and/or upper cartridges (120, 160). Merely exemplary adjunct deployment mechanisms that may be incorporated into lower and/or upper cartridges (120, 160) are described in U.S. patent application Ser. No. 13/206,752, entitled "Device for Applying Adjunct in Endoscopic Procedure," filed Aug. 10, 2011, and published Feb. 14, 2013 as U.S. Pat. Pub. No. 2013/0037596; U.S. patent application Ser. No. 13/206,725, entitled "Surgical Staple with Localized Adjunct Coating," filed Aug. 10, 2011, and published Feb. 14, 2013 as U.S. Pat. Pub. No. 2013/0041406; U.S. patent application Ser. No. 13/233,633, entitled "Fibrin Pad Matrix with Suspended Heat Activated Beads of Adhesive," filed Sep. 15, 2011, and issued Aug. 26, 2014 as U.S. Pat. No. 8,814,025; U.S. patent application Ser. No. 13/233,646, entitled "Surgical Instrument with Filled Staple," filed Sep. 15, 2011, and published Mar. 21, 2013 as U.S. Pat. Pub. No. 2013/0068815; U.S. patent application Ser. No. 13/230,994, entitled "Resistive Heated Surgical Staple Cartridge with Phase Change Sealant," filed Sep. 13, 2011, published Mar. 14, 2013 as U.S. Pat. Pub. No. 2013/0062393, and issued on Apr. 7, 2015 as U.S. Pat. No. 8,998,060; U.S. patent application Ser. No. 13/195,170, entitled "Adjunct Therapy Device Having Driver with Cavity for Hemostatic Agent," filed Aug. 1, 2011, published Feb. 7, 2013 as U.S. Pat. Pub. No. 2013/0032626, and issued on Apr. 7, 2015 as U.S. Pat. No. 8,998,059; U.S. patent application Ser. No. 13/240,141, entitled "Adjunct Therapy Device for Applying Hemostatic Agent," filed Sep. 22, 2011, and published Mar. 28, 2013 as U.S. Pat. Pub. No. 2013/0075447; U.S. patent application Ser. No. 13/242,164, entitled "Surgical Stapling Device with Adjunct Material Application Feature," filed Sep. 23, 2011, published Mar. 28, 2013 as U.S. Pat. Pub. No. 2013/0075451, and issued on Mar. 24, 2015 as U.S. Pat. No. 8,985,429; and U.S. patent application Ser. No. 13/240,074, entitled "Surgical Staple Assembly with Hemostatic Feature," filed Sep. 22, 2011, and published Mar. 28, 2013 as U.S. Pat. Pub. No. 2013/0075446; the disclosures of which are incorporated by reference herein.

Furthermore, while end effector (100) described herein advanced firing bar (14) distally prior to lower and upper wedge sleds (192, 196), it should be understood that lower and upper wedge sleds (192, 196) may precede firing bar (14) and/or cutting edge (48). For instance, lower and upper wedge sleds (192, 196) may include a central member (not shown) that cams actuation members (142, 182) outwardly relative to the central member. Accordingly, lower and upper wedge sleds (192, 196) may both vertically orient staple drivers (140, 180) and cam staple drivers (140, 180) vertically via ramped members (194, 198). Thus, tissue (90) may initially be stapled prior to severance by cutting edge (48). In still another version, lower and upper wedge sleds (192, 196) may be substantially longitudinally aligned with cutting edge (48) such that the severance and stapling of tissue (90) occurs substantially simultaneously. Still other configurations for end effector (100), lower cartridge (120) and/or upper cartridge (160) will be apparent to one of ordinary skill in the art in view of the teachings herein.

B. Exemplary Stamped Dual Staple Cartridges

Figure 8A:
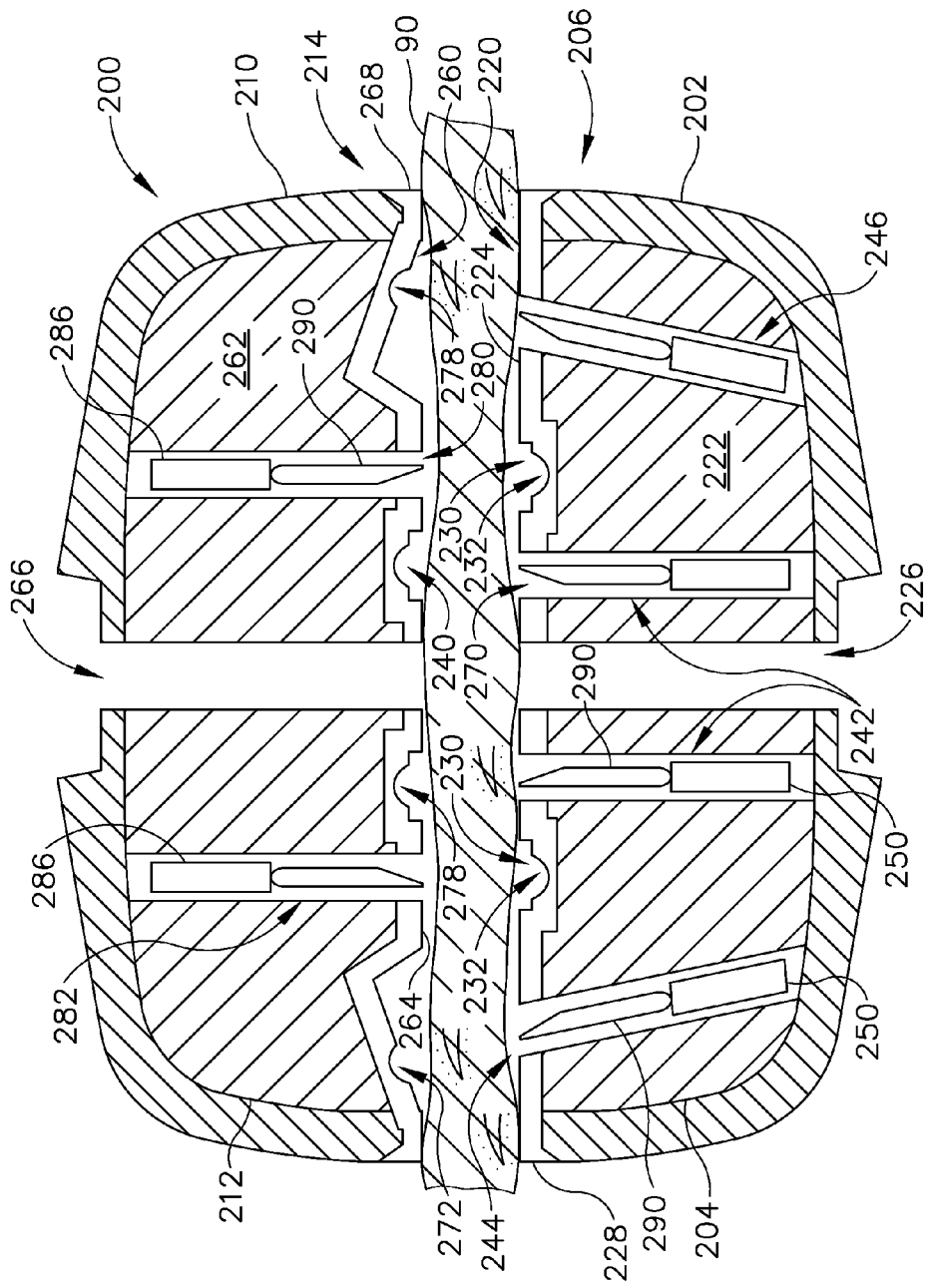
FIG. 8A depicts a front elevation cross-sectional view of an exemplary alternative end effector having an exemplary alternative lower cartridge and upper cartridge.
Figure 8B:
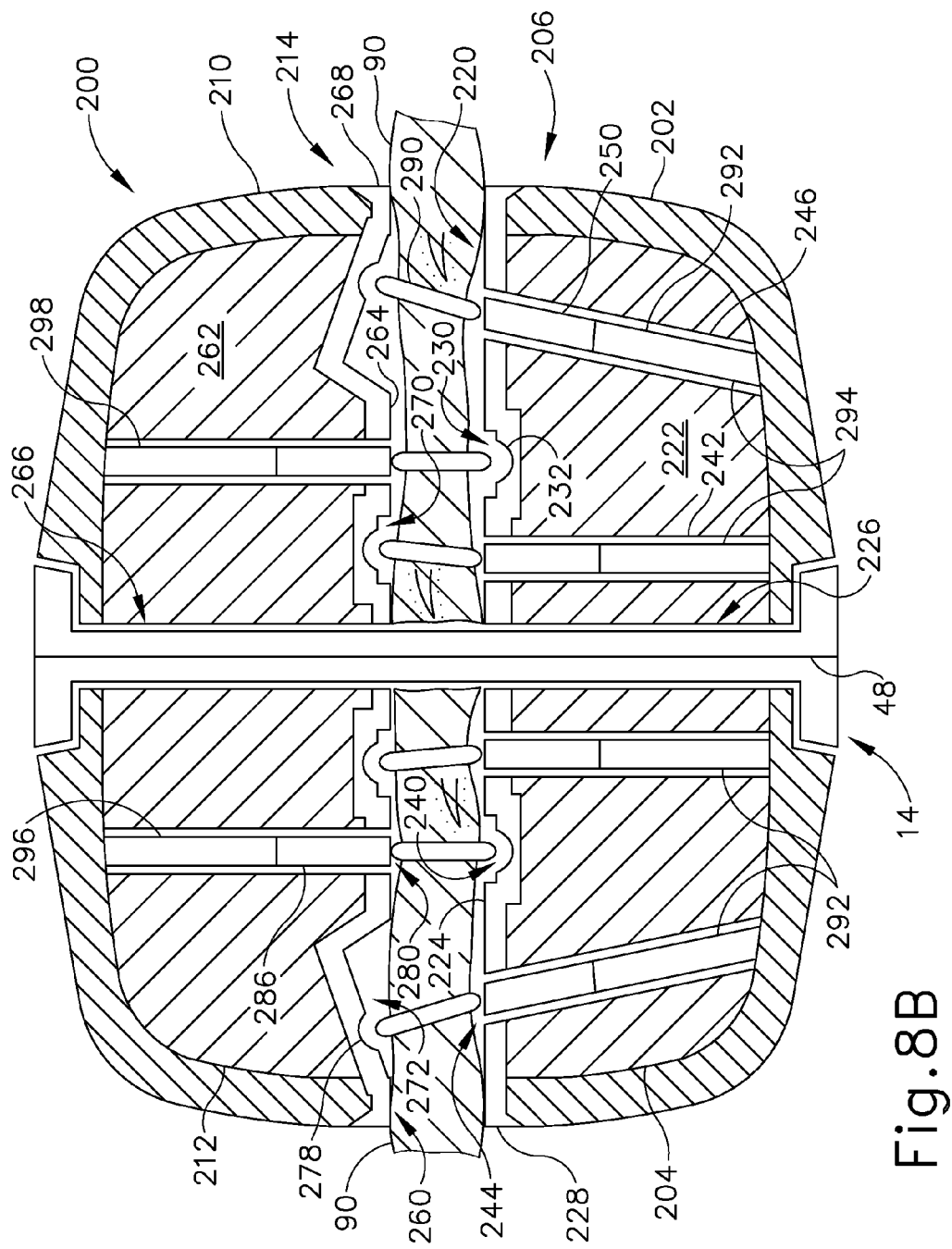
FIG. 8B depicts a front elevation cross-sectional view of the end effector of FIG. 8A, showing an exemplary upper wedge sled and lower wedge sled camming the staple drivers.

FIGS. 8A-8B depict an exemplary alternative end effector (200) configured to receive a lower cartridge (220) and an upper cartridge (260). It should be understood that instrument (10) may be readily modified to incorporate end effector (200). In the present example, end effector (200) includes a lower jaw (202) and a pivotable upper jaw (210). End effector (200) is coupled to handle portion (20), described above. In particular, a clinician may pivotally draw closure trigger (26) toward pistol grip (24) to cause clamping, or closing, of the upper jaw (210) toward lower jaw (202) of end effector (200). In the present example, lower jaw (202) defines a lower recess (204) configured to receive lower cartridge (220). Lower jaw (202) further includes a rim (206) that is configured to receive a resilient lower lip (228) of lower cartridge (220) such that lower cartridge (220) is selectively coupleable to lower jaw (202). In addition or in the alternative, lower jaw (202) may include an open distal end and longitudinal rails (not shown) onto or below which lower cartridge (220) may be slid. Lower jaw (202) and/or lower cartridge (220) may include detents or snap features at a distal end to selectively couple lower cartridge (220) to lower jaw (202) when lower cartridge (220) is slid proximally along the longitudinal rails. Still further, lower jaw (202) may have detents (not shown) similar to detents (106) shown in FIGS. 7A-7C. Of course other configurations for inserting and coupling lower cartridge (220) to lower jaw (202) will be apparent to one of ordinary skill in the art in view of the teachings herein.

Upper jaw (210) defines an upper recess (212) configured to receive upper cartridge (260). Upper jaw (210) further includes a rim (214) that is configured to receive a resilient upper lip (268) of upper cartridge (220) such that upper cartridge (220) is selectively coupleable to upper jaw (210). In addition or in the alternative, upper jaw (210) may include an open distal end and longitudinal rails (not shown) onto or above which upper cartridge (260) may be slid. Upper jaw (210) and/or upper cartridge (260) may include detents or snap features at a distal end to selectively couple upper cartridge (260) to upper jaw (210) when upper cartridge (260) is slid proximally along the longitudinal rails. Still further, upper jaw (210) may have detents (not shown) similar to detents (114) shown in FIGS. 7A-7C. Of course other configurations for inserting and coupling upper cartridge (260) to upper jaw (210) will be apparent to one of ordinary skill in the art in view of the teachings herein.

Lower cartridge (220) of the present example comprises a cartridge body (222), an upper deck (224), a plurality of interior staple apertures (240), a plurality of exterior staple apertures (244), a plurality of staple drivers (250), a vertical slot (226), and a resilient lower lip (228). Lower cartridge (220) may be further constructed in accordance with at least some of the teachings of cartridges (37, 120, 160, 260) described herein. In the present example, resilient lower lip (228) is operable to selectively couple lower cartridge (220) to lower jaw (202) by an interference fit. As shown in FIG. 8A, upper deck (224) includes vertical slot (226) formed along a longitudinal axis of lower cartridge (220) and four staple apertures (240, 244) formed therein—an exterior staple aperture (244) and an interior staple aperture (240) formed on each side of vertical slot (226). It should be understood that the four staple apertures (240, 244) are a part of four rows of staple apertures (240, 244) extending longitudinally along lower cartridge (220). Moreover, any number of rows of staple apertures (240, 244) may be formed in upper deck (224), and the four rows of staple apertures (240, 244) are merely exemplary. Further still, staple apertures (240, 244) may be disposed about vertical slot (226) in other configurations. For instance, staple apertures (240, 244) may be symmetrically disposed about vertical slot (226) or staple apertures (240, 244) may be asymmetrically disposed about vertical slot (226). By way of example only, for a curved end effector (200), a single exterior staple aperture (244) and two interior staple apertures (240) may be disposed on one side of vertical slot (226) and a single exterior staple aperture (244) may be disposed on the opposing side.

In the present example, inner staple apertures (240) are in communication with substantially vertical recesses (242) having a staple driver (250) therein. Exterior staple apertures (244) are in communication with angled recesses (246) formed at an angle relative to upper deck (224) and also having a staple driver (250) therein. The angle of angled recesses (246) may be from 0 degrees to 90 degrees, inclusive. In the example shown, angled recesses (246) are disposed at an angle of approximately 15 degrees, though this is merely illustrative. It should be understood that longer staples (290) may be included in lower cartridge (220) due to the angling of staples (290). In other words, lower cartridge (220) may accommodate relatively larger staples (290) than cartridge (37), without having to increase the outer diameter of end effector (200). Furthermore, lower jaw (202) and upper jaw (210) may be sized to permit more tissue (90) and/or buttress material (not shown) therebetween due to the reduced lower cartridge (220) size.

Upper deck (224) of the present example further comprises a plurality of stamped recesses (230) having staple forming pockets (232) formed therein. Staple forming pockets (232) are configured to receive and bend portions of staples (290) that are cammed via staple drivers (286) of upper cartridge (260), as will be described in more detail below. In the present example, stamped recesses (230) are substantially vertical recesses corresponding to the vertical staple apertures (280) and recesses (282) of upper cartridge (260), though this is merely optional. Indeed, in some versions stamped recesses (230) may be angled relative to upper deck (224) in a similar configuration to exterior stamped recesses (272) described below. Of course other configurations and orientations for stamped recesses (230) will be apparent to one of ordinary skill in the art in view of the teachings herein. Vertical slot (226) extends longitudinally through upper deck (224) and cartridge body (222) such that firing bar (14) is actuatable therethrough. In some versions vertical slot (226) is a longitudinally straight slot while in other versions vertical slot (226) may be curved along the longitudinal axis for a curved end effector (200).

Staple drivers (250) of the present example are disposed within cartridge body (222) and are vertically movable members within lower cartridge (220). In some versions staple drivers (250) are selectively coupled within recesses (242, 246) such that staple drivers (250) are prevented from inadvertently actuating relative to cartridge body (222) until a lower wedge sled (292), described below, engages staple drivers (250). For instance, staple drivers (250) may be adhesively attached to cartridge body (222). In other versions, staple drivers (250) may each include a tab (not shown) that is insertable into a slot (not shown) formed in cartridge body (222) such that an interference fit or detent fit is formed. Accordingly, staple drivers (250) are selectively secured relative to cartridge body (222) even if the user rotates or inverts end effector (200). Of course other selectively coupleable configurations will be apparent to one of ordinary skill in the art in view of the teachings herein.

In the present example, a plurality of staples (290) are also disposed within cartridge body (222) and are disposed above corresponding staple drivers (250). In particular, each staple (290) is driven vertically within cartridge body (222) by a respective staple driver (250) to drive staple (290) out through an associated staple aperture (240, 244). In some versions staples (290) are selectively coupled to staple drivers (250) such that staples (290) are prevented from inadvertently actuating relative to staple drivers (250) until lower wedge sled (292), described below, engages staple drivers (250) to expel staples (290) out of staple apertures (240, 244). For instance, staples (290) may be adhesively attached to staple drivers (250). In other versions, staples (290) may each include a tab (not shown) that is insertable into a slot (not shown) formed in staple drivers (250) such that an interference fit is formed. Further still, a snap feature may be included on staple drivers (250) to retain staple (290) with staple driver (250) until deployed. In some versions, staple drivers (250) may include a release tab (not shown) that engages a tab (not shown) on cartridge body (222) to release staple (290) as staple drivers (250) are actuated vertically. Such a tab on cartridge body (222) may be at or near upper deck (224) such that staples (290) are released only when staple driver (250) is at its vertical actuation peak. Accordingly, staples (290) are selectively secured relative to staple drivers (250) even if the user rotates or inverts end effector (200). In addition to or in lieu of being secured to staple drivers (250), staples (290) may be selectively secured to cartridge body (222), such as by an interference fit and/or otherwise through friction.

Upper cartridge (260) of the present example comprises a cartridge body (262), a lower deck (264), a plurality of upper staple apertures (280), a plurality of staple drivers (286), a vertical slot (266), and a resilient upper lip (268). Upper cartridge (260) may be further constructed in accordance with at least some of the teachings of cartridges (37, 120, 160, 220) described herein. In the present example, resilient upper lip (268) is operable to selectively couple upper cartridge (260) to upper jaw (210) by an interference fit. As shown in FIG. 8A, lower deck (264) includes vertical slot (266) formed along a longitudinal axis of upper cartridge (260) and two upper staple apertures (280) formed on each side of vertical slot (266). It should be understood that the two staple apertures (280) are a part of two rows of staple apertures (280) extending longitudinally along upper cartridge (260), though any number of staple apertures (280) may be formed in lower deck (264), and the two staple apertures (280) shown are merely exemplary. Further still, staple apertures (280) may be disposed about vertical slot (266) in various configurations. For instance, both staple apertures (280) may be disposed on one side of vertical slot (266) for a curved end effector (200).

In the present example, upper staple apertures (280) are in communication with substantially vertical recesses (282) having a staple driver (286) therein. Of course, alternatively, recesses (282) and staple apertures (280) may be configured in accordance with exterior staple apertures (244) and/or angled recesses (246) described above.

Lower deck (264) of the present example further comprises a plurality of stamped recesses (270, 272) having staple forming pockets (278) formed therein. Staple forming pockets (278) are configured to receive and bend portions of staples (290) that are cammed via staple drivers (250) of lower cartridge (220), as described above. In the present example, lower deck (264) includes a pair of interior stamped recesses (270) and a pair of exterior, or "coined," stamped recesses (272). Interior stamped recesses (270) comprise substantially vertical recesses corresponding to the interior staple apertures (240) and recesses (242) of lower cartridge (220), though this is merely optional. Exterior stamped recesses (272) comprise angled recesses corresponding to exterior staple apertures (244) and angled recesses (246) of lower cartridge (220). Of course other configurations and orientations for stamped recesses (270, 272) will be apparent to one of ordinary skill in the art in view of the teachings herein. Vertical slot (266) extends longitudinally through lower deck (264) and cartridge body (262) such that firing bar (14) is actuatable therethrough. In some versions vertical slot (266) is a longitudinally straight slot while in other versions vertical slot (266) may be curved along the longitudinal axis for a curved end effector (200).

Staple drivers (286) of the present example are disposed within cartridge body (262) and are vertically movable members within upper cartridge (260). In some versions staple drivers (286) are selectively coupled within vertical recesses (282) such that staple drivers (286) are prevented from inadvertently actuating relative to cartridge body (262) until an upper wedge sled (296), described below, engages staple drivers (286). For instance, staple drivers (286) may be adhesively attached to cartridge body (262). In other versions, staple drivers (286) may each include a tab (not shown) that is insertable into a slot (not shown) formed in cartridge body (262) such that an interference fit is formed. Accordingly, staple drivers (286) are selectively secured relative to cartridge body (262) even if the user rotates or inverts end effector (200). Of course other selectively coupleable configurations will be apparent to one of ordinary skill in the art in view of the teachings herein.

In the present example, a plurality of staples (290) are also disposed within cartridge body (262) and are disposed below corresponding staple drivers (286), as shown in FIG. 8A. In particular, each staple (290) is driven vertically within cartridge body (262) by a respective staple driver (286) to drive staple (290) out through an associated staple aperture (280). In some versions staples (290) are selectively coupled to staple drivers (286) such that staples (290) are prevented from inadvertently actuating relative to staple drivers (286) until upper wedge sled (296), described below, engages staple drivers (286) to expel staples (290) out of staple apertures (280). For instance, staples (290) may be adhesively attached to staple drivers (286). In other versions, staples (290) may each include a tab (not shown) that is insertable into a slot (not shown) formed in staple drivers (286) such that an interference fit is formed. Further still, a snap feature may be included on staple drivers (286) to retain staple (290) with staple driver (286) until deployed. In some versions, staple drivers (286) may include a release tab (not shown) that engages a tab (not shown) on cartridge body (262) to release staple (290) as staple drivers (286) are actuated. Such a tab on cartridge body (262) may be at or near lower deck (264) such that staples (290) are released only when staple driver (286) is at the end of its actuation movement. Accordingly, staples (290) are selectively secured relative to staple drivers (286) such that staples (290) do not disengage from staple drivers (286) due to the force of gravity. In addition to or in lieu of being secured to staple drivers (286), staples (290) may be selectively secured to cartridge body (262), such as by an interference fit and/or otherwise through friction.

FIGS. 8A-8B depict the firing of firing bar (14) through lower and upper cartridges (220, 260) to deploy staples (290) into tissue (90). As shown in FIG. 8A, tissue (90) is secured between lower jaw (202) and upper jaw (210) after closure trigger (26) has been actuated. In this initial position, staple drivers (250, 286) have not been engaged by lower or upper wedge sleds (292, 296). As mentioned previously, frame (34) longitudinally slidingly supports a firing drive member that extends through shaft (23) and communicates a firing motion from firing trigger (28) to firing bar (14), as shown in FIGS. 1-5. When firing trigger (28) is actuated by a user, firing bar (14) advances distally relative to handle portion (20). As firing bar (14) is advanced distally, a pair of pusher blocks (not shown), such as pusher blocks (80) described above, each engage a respective wedge sled (292, 296) such that wedge sleds (292, 296) are pushed distally by the pusher blocks as firing bar (14) is advanced distally through upper and lower cartridges (220, 260). As wedge sleds (292, 296) are actuated distally, each wedge sled (292, 296) engages the set of respective staple drivers (250, 286) to upwardly cam staple drivers (250) and downwardly cam staple drivers (286). In turn, staple drivers (250, 286) drive staples (290) out through a respective staple aperture (240, 244, 280), through tissue (90), and into forming contact with a respective staple forming pocket (232, 278) in a respective stamped recess (230, 270, 272). In the present example, lower wedge sled (292) comprises four ramped members (294) (two vertical interior ramped members (294) and two angled exterior ramped members (294)) configured to cam staple drivers (250) toward upper deck (224). Upper wedge sled (296) comprises two ramped members (298) configured to cam staple drivers (286) toward lower deck (264). Of course other configurations for lower wedge sled (292) and/or upper wedge sled (296) will be apparent to one of ordinary skill in the art in view of the teachings herein.

As shown in FIG. 8B, cutting edge (48) of firing bar (14) also advances distally as wedge sleds (292, 296) are advanced distally. In some versions, cutting edge (48) simultaneously severs tissue (90) as wedge sleds (292, 296) engage and cam staple drivers (250, 286), though this is merely optional. Indeed, cutting edge (48) may be configured to sever tissue (90) prior to the camming of staple drivers (250, 286) or after the camming of staple drivers (250, 286). As also shown in FIG. 8B, firing bar (14) includes a pair of flanges on the top and bottom ends of firing bar (14) that slide along exterior channels of the bottom and upper jaws (202, 210). As will be apparent to one of ordinary skill in the art, the flanges cooperatively compress bottom and upper jaws (202, 210) together to further secure tissue (90) therebetween as firing bar (14) is actuated distally.

When lower wedge sled (292) is advanced distally, staple drivers (250) are cammed such that staples (290), driven by staple drivers (250), are extended out of staple apertures (240, 244) of lower cartridge (220). Staples (290) pierce through tissue (90) and enter stamped recesses (270, 272) to engage staple forming pockets (278) formed in lower deck (264) of upper cartridge (260). Accordingly, staples (290) are bent and staple tissue (90). Similarly, when upper wedge sled (296) is advanced distally, staple drivers (286) are cammed such that staples (290), driven by staple drivers (286), are extended out of staple apertures (280) of upper cartridge (260). Staples (290) pierce through tissue (90) and enter stamped recesses (230) to engage staple forming pockets (232) formed in upper deck (224) of lower cartridge (220). Accordingly, staples (290) are bent and staple tissue (90). As shown in FIG. 8B, opposingly oriented staples (290) are stapled through tissue (90) using the present end effector (200) having a lower and upper cartridge (220, 260). The user may then release firing trigger (28) and closure trigger (26) to release the stapled tissue (90). The user may then replace lower and upper cartridges (220, 260) with new lower and upper cartridges (220, 260) to staple a new section of tissue (90).

Of course, other configurations for end effector (200), lower cartridge (220) and/or upper cartridge (260) will be apparent to one of ordinary skill in the art in view of the teachings herein. For instance, in some versions a buttress material (not shown) may be coupled to lower cartridge (220) and/or upper cartridge (260). Merely exemplary configurations for lower cartridge (220) and/or upper cartridge (260) having a buttress material are described in various references that are cited and incorporated by reference herein. In addition, or in some versions in the alternative, an adjunct material (e.g., an adhesive, a therapeutic agent, etc.) may be applied to tissue (90) via lower and/or upper cartridges (220, 260). Merely exemplary adjunct deployment mechanisms that may be incorporated into lower and/or upper cartridges (220, 260) are described in various references that are cited and incorporated by reference herein. Still other suitable configurations for end effector (200), lower cartridge (220), and/or upper cartridge (260) will be apparent to one of ordinary skill in the art in view of the teachings herein.

While certain configurations of exemplary surgical instruments have been described, various other ways in which the surgical instruments may be configured will be apparent to those of ordinary skill in the art in view of the teachings herein. By way of example only, the surgical instruments referred to herein may be constructed in accordance with at least some of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; and U.S. Pat. No. 7,721,930.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) an instrument comprising:
        i. a body portion, and
        ii. an end effector extending proximally from the body portion, wherein the end effector comprises a lower jaw and a upper jaw;
    (b) a lower staple cartridge insertable into the lower jaw of the end effector, the lower staple cartridge comprising:
        i. a first cartridge body having an upper deck, the upper deck comprising a first plurality of staple apertures formed therein,
        ii. a first plurality of staple drivers movable relative to the first cartridge body, wherein at least one staple driver of the first plurality of staple drivers is pivotably coupled to an actuation member, and iii. a first plurality of staples in communication with the first plurality of staple drivers, wherein the first plurality of staples are movable relative to the first cartridge body; and (c) an upper staple cartridge insertable into the upper jaw of the end effector, the upper staple cartridge comprising:
  i. a second cartridge body having an lower deck, the lower deck comprising a second plurality of staple apertures formed therein,
  ii. a second plurality staple drivers movable relative to the second cartridge body, and
  iii. a second plurality of staples in communication with the second plurality of staple drivers, wherein the second plurality of staples are movable relative to the second cartridge body.

2. The apparatus of claim 1 wherein the first plurality of staple drivers are disposed at an angle relative to the upper deck, and wherein the first plurality of staple drivers are at a non-perpendicular angle relative to the upper deck.

3. The apparatus of claim 1 wherein the actuation member is operable to pivot the at least one staple driver to a position in which the at least one staple driver is substantially perpendicular relative to the upper deck.

4. The apparatus of claim 3 wherein the instrument further comprises a longitudinally actuatable firing bar, wherein the firing bar is operable to laterally actuate the actuation member relative to the first cartridge body.

5. The apparatus of claim 1 wherein the upper deck further comprises a vertical slot, wherein the vertical slot extends longitudinally through a portion of the upper deck, and wherein the vertical slot defines a first side of the upper deck and a second side of the upper deck.

6. The apparatus of claim 5 wherein a first staple driver of the first plurality of staple drivers is disposed below the first side of the upper deck and wherein a second staple driver of the first plurality of staple drivers is disposed below the second side of the upper deck.

7. The apparatus of claim 6 wherein the first staple driver is pivotably coupled to a first actuation member, wherein the second staple driver is pivotably coupled to a second actuation member.

8. The apparatus of claim 7 wherein the first actuation member is operable to pivot the first staple driver to a position in which the first staple driver is substantially perpendicular relative to the upper deck and wherein the second actuation member is operable to pivot the second staple driver to a position in which the second staple driver is substantially perpendicular relative to the upper deck.

9. The apparatus of claim 1 wherein the upper deck of the lower staple cartridge comprises a set of staple forming pockets, wherein the second plurality of staple drivers are operable to actuate the second plurality of staples into communication with the plurality of staple forming pockets.

10. The apparatus of claim 1 wherein the lower staple cartridge comprises a lower wedge sled and wherein the lower wedge sled is operable to drive the first plurality of staple drivers relative to the first cartridge body.

11. The apparatus of claim 1 wherein the second plurality of staple drivers are disposed at an angle relative to the lower deck, and wherein the second plurality of staple drivers are at a non-perpendicular angle relative to the lower deck.

12. The apparatus of claim 1 wherein the instrument comprises a closure trigger, wherein the closure trigger is operable to pivot the upper jaw relative to the lower jaw.

13. The apparatus of claim 1 wherein the instrument comprises a firing trigger, wherein the firing trigger is operable to actuate the first plurality of staple drivers and the second plurality of staple drivers.

14. The apparatus of claim 1 wherein the lower deck of the upper staple cartridge comprises a plurality of staple forming pockets, wherein the first plurality of staple drivers are operable to actuate the first plurality of staples into communication with the plurality of staple forming pockets.

15. A staple cartridge comprising:
(a) a cartridge body having an upper deck, the upper deck comprising:
  i. a plurality of staple apertures formed through the upper deck, and
  ii. a vertical slot longitudinally extending through at least part of the cartridge body, wherein the vertical slot defines a first side of the cartridge body and a second side of the cartridge body;
(b) a first staple driver disposed within the first side of the cartridge body, wherein the first staple driver is movable relative to the upper deck;
(c) a second staple driver disposed within the second side of the cartridge body, wherein the second staple driver is movable relative to the upper deck;
(d) a first staple in communication with the first staple driver;
(e) a second staple in communication with the second staple driver;
wherein the first staple driver is configured to pivot between a positive oblique orientation and a perpendicular orientation relative to the upper deck;
wherein the second staple driver is configured to pivot between a negative oblique orientation and a perpendicular orientation relative to the upper deck.

16. The staple cartridge of claim 15 wherein the first staple driver is pivotably coupled to a first actuation member, wherein the second staple driver is pivotably coupled to a second actuation member, wherein the first actuation member and the second actuation member are operable to pivot the first staple driver and the second staple driver to the perpendicular orientation relative to the upper deck.

17. The staple cartridge of claim 16 further comprising a wedge sled disposed within the cartridge body, wherein the wedge sled is operable to actuate the first actuation member and the second actuation member.

18. An apparatus comprising:
(a) an instrument comprising:
  i. a body portion, and
  ii. an end effector extending proximally from the body portion, wherein the end effector comprises a lower jaw and a upper jaw;
(b) a lower staple cartridge insertable into the lower jaw of the end effector, the lower staple cartridge comprising:
  i. a first cartridge body having an upper deck, the upper deck comprising a first plurality of staple apertures formed therein, the upper deck further comprising a plurality of staple forming pockets,
  ii. a first plurality of staple drivers movable relative to the first cartridge body, and
  iii. a first plurality of staples in communication with the first plurality of staple drivers, wherein the first plurality of staples are movable relative to the first cartridge body; and
(c) an upper staple cartridge insertable into the upper jaw of the end effector, the upper staple cartridge comprising:
  i. a second cartridge body having an lower deck, the lower deck comprising a second plurality of staple apertures formed therein, the lower deck further comprising a plurality of staple forming pockets, wherein the staple forming pockets are oriented at an angle relative to the lower deck, wherein the first plurality of staple drivers of the lower staple cartridge are operable to actuate the first plurality of staples into communication with the plurality of staple forming pockets of the upper staple cartridge, ii. a second plurality staple drivers movable relative to the second cartridge body, and iii. a second plurality of staples in communication with the second plurality of staple drivers, wherein the second plurality of staples are movable relative to the second cartridge body, wherein the second plurality of staple drivers are operable to actuate the second plurality of staples into communication with the plurality of staple forming pockets of the lower staple cartridge.

* * * * *